(12) United States Patent
Kubacki et al.

(10) Patent No.: US 12,114,872 B2
(45) Date of Patent: Oct. 15, 2024

(54) ALIGNMENT GUIDE, SYSTEMS, AND METHODS

(71) Applicant: Wright Medical Technology, Inc., Memphis, TN (US)

(72) Inventors: Meghan R. Kubacki, Cookeville, TN (US); Jerry W. West, Arlington, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 329 days.

(21) Appl. No.: 17/650,888

(22) Filed: Feb. 14, 2022

(65) Prior Publication Data

US 2022/0313283 A1 Oct. 6, 2022

Related U.S. Application Data

(60) Provisional application No. 63/167,926, filed on Mar. 30, 2021.

(51) Int. Cl.
*A61B 17/17* (2006.01)
*A61B 17/56* (2006.01)

(52) U.S. Cl.
CPC ........ *A61B 17/17* (2013.01); *A61B 2017/564* (2013.01); *A61B 2017/568* (2013.01)

(58) Field of Classification Search
CPC .............. A61B 17/17; A61B 2017/564; A61B 2017/568
See application file for complete search history.

(56) References Cited

U.S. PATENT DOCUMENTS

| | | | |
|---|---|---|---|
| 3,839,742 | A | 10/1974 | Link |
| 3,872,519 | A | 3/1975 | Giannestras et al. |
| 3,886,599 | A | 6/1975 | Schlein |
| 3,889,300 | A | 6/1975 | Smith |
| 3,896,502 | A | 7/1975 | Lennox |
| 3,896,503 | A | 7/1975 | Freeman et al. |
| 3,975,778 | A | 8/1976 | Newton, III |

(Continued)

FOREIGN PATENT DOCUMENTS

| | | |
|---|---|---|
| GB | 2480846 | 12/2011 |
| JP | H11-500035 A | 1/1999 |

(Continued)

OTHER PUBLICATIONS

Search report for EP 13198280 dated Feb. 5, 2014.

(Continued)

*Primary Examiner* — Sameh R Boles
(74) *Attorney, Agent, or Firm* — DUANE MORRIS LLP

(57) ABSTRACT

An alignment guide includes a base, a swing arm for coupling to the base such that the swing arm is movable relative to the base, and a locking device for selectively fixing a position of the swing arm relative to the base. The base defines at least one first hole sized and configured to receive a first fixation element and defines at least one second hole sized and configured to receive a second fixation element. The swing arm extends from a first end to a second end. The second end of the swing arm including a coupling mechanism for coupling another guide to the second end of the swing arm. Methods also are disclosed.

20 Claims, 15 Drawing Sheets

(56) References Cited

U.S. PATENT DOCUMENTS

| | | |
|---|---|---|
| 3,987,500 A | 10/1976 | Schlein |
| 4,021,864 A | 5/1977 | Waugh |
| 4,069,518 A | 1/1978 | Groth, Jr. |
| 4,156,944 A | 6/1979 | Schreiber et al. |
| 4,166,292 A | 9/1979 | Bokros |
| 4,204,284 A | 5/1980 | Koeneman |
| 4,232,404 A | 11/1980 | Samuelson et al. |
| 4,309,778 A | 1/1982 | Buechel et al. |
| 4,470,158 A | 9/1984 | Pappas et al. |
| 4,755,185 A | 7/1988 | Tarr |
| 4,968,316 A | 11/1990 | Hergenroeder |
| 5,041,139 A | 8/1991 | Bránemark |
| 5,312,412 A | 5/1994 | Whipple |
| 5,326,365 A | 7/1994 | Alvine |
| 5,354,300 A | 10/1994 | Goble et al. |
| 5,364,401 A * | 11/1994 | Ferrante ............ A61B 17/1659 606/88 |
| 5,423,825 A | 6/1995 | Levine |
| 5,476,466 A | 12/1995 | Barrette et al. |
| 5,601,563 A | 2/1997 | Burke et al. |
| 5,628,749 A | 5/1997 | Vendrely et al. |
| 5,634,927 A | 6/1997 | Houston et al. |
| 5,735,904 A | 4/1998 | Pappas |
| 5,766,259 A | 6/1998 | Sammarco |
| 5,776,200 A | 7/1998 | Johnson et al. |
| 5,817,097 A | 10/1998 | Howard et al. |
| 5,824,106 A | 10/1998 | Fournal |
| 5,879,389 A | 3/1999 | Koshino |
| 5,885,299 A | 3/1999 | Winslow et al. |
| 5,888,203 A | 3/1999 | Goldberg |
| 5,897,559 A | 4/1999 | Masini |
| 5,935,132 A | 8/1999 | Bettuchi et al. |
| 6,002,859 A | 12/1999 | DiGioia, III et al. |
| 6,033,405 A | 3/2000 | Winslow et al. |
| 6,102,952 A | 8/2000 | Koshino |
| 6,183,519 B1 | 2/2001 | Bonnin et al. |
| 6,245,109 B1 | 6/2001 | Mendes et al. |
| 6,342,056 B1 | 1/2002 | Mac-Thiong et al. |
| 6,409,767 B1 | 6/2002 | Pericé et al. |
| 6,436,146 B1 | 8/2002 | Hassler et al. |
| 6,478,800 B1 | 11/2002 | Fraser et al. |
| 6,520,964 B2 | 2/2003 | Tallarida et al. |
| 6,530,930 B1 | 3/2003 | Marino et al. |
| 6,610,067 B2 | 8/2003 | Tallarida et al. |
| 6,610,095 B1 | 8/2003 | Pope et al. |
| 6,620,168 B1 | 9/2003 | Lombardo et al. |
| 6,645,215 B1 | 11/2003 | McGovern et al. |
| 6,663,669 B1 | 12/2003 | Reiley |
| 6,673,116 B2 | 1/2004 | Reiley |
| 6,679,917 B2 | 1/2004 | Ek |
| 6,719,799 B1 | 4/2004 | Kropf |
| 6,824,567 B2 | 11/2004 | Tornier et al. |
| 6,852,130 B2 | 2/2005 | Keller et al. |
| 6,860,902 B2 | 3/2005 | Reiley |
| 6,863,691 B2 | 3/2005 | Short et al. |
| 6,875,222 B2 | 4/2005 | Long et al. |
| 6,875,236 B2 | 4/2005 | Reiley |
| 6,926,739 B1 | 8/2005 | O'Connor et al. |
| 6,939,380 B2 | 9/2005 | Guzman |
| 6,942,670 B2 | 9/2005 | Heldreth et al. |
| 7,001,394 B2 | 2/2006 | Gundlapalli et al. |
| 7,011,687 B2 | 3/2006 | Deffenbaugh |
| 7,025,790 B2 | 4/2006 | Parks et al. |
| 7,163,541 B2 | 1/2007 | Ek |
| 7,238,190 B2 | 7/2007 | Schon et al. |
| 7,252,684 B2 | 8/2007 | Dearnaley |
| 7,314,488 B2 | 1/2008 | Reiley |
| 7,323,012 B1 | 1/2008 | Stone et al. |
| 7,476,227 B2 | 1/2009 | Tornier et al. |
| 7,481,814 B1 | 1/2009 | Metzger |
| 7,485,147 B2 | 2/2009 | Papps et al. |
| 7,534,246 B2 | 5/2009 | Reiley et al. |
| 7,618,421 B2 | 11/2009 | Axelson, Jr. et al. |
| 7,625,409 B2 | 12/2009 | Saltzman et al. |
| 7,641,697 B2 | 1/2010 | Reiley |
| 7,678,151 B2 | 3/2010 | Ek |
| 7,713,305 B2 | 5/2010 | Ek |
| 7,717,920 B2 | 5/2010 | Reiley |
| 7,763,080 B2 | 7/2010 | Southworth |
| 7,803,158 B2 | 9/2010 | Hayden |
| 7,850,698 B2 | 12/2010 | Straszheim-Morley et al. |
| 7,896,883 B2 | 3/2011 | Ek et al. |
| 7,896,885 B2 | 3/2011 | Miniaci et al. |
| 7,909,882 B2 | 3/2011 | Stinnette |
| 7,963,996 B2 | 6/2011 | Saltzman et al. |
| 8,002,841 B2 | 8/2011 | Hasselman |
| 8,012,217 B2 | 9/2011 | Strzepa et al. |
| 8,034,114 B2 | 10/2011 | Reiley |
| 8,034,115 B2 | 10/2011 | Reiley |
| 8,048,164 B2 | 11/2011 | Reiley |
| 8,110,006 B2 | 2/2012 | Reiley |
| 8,114,091 B2 | 2/2012 | Ratron et al. |
| 8,167,888 B2 | 5/2012 | Steffensmeier |
| 8,172,850 B2 | 5/2012 | McMinn |
| 8,177,841 B2 | 5/2012 | Ek |
| 8,268,007 B2 | 9/2012 | Barsoum et al. |
| 8,303,667 B2 | 11/2012 | Younger |
| 8,313,492 B2 | 11/2012 | Wong et al. |
| 8,323,346 B2 | 12/2012 | Tepic |
| 8,337,503 B2 | 12/2012 | Lian |
| 8,361,159 B2 | 1/2013 | Ek |
| 8,475,463 B2 | 7/2013 | Lian |
| 8,491,596 B2 | 7/2013 | Long et al. |
| 8,808,303 B2 | 8/2014 | Stemniski et al. |
| 2002/0082607 A1 | 6/2002 | Heldreth et al. |
| 2002/0133164 A1 | 9/2002 | Williamson |
| 2002/0173853 A1 | 11/2002 | Corl, III et al. |
| 2003/0208280 A1 | 11/2003 | Tohidi |
| 2003/0236522 A1 | 12/2003 | Long et al. |
| 2004/0030399 A1 | 2/2004 | Asencio |
| 2004/0039394 A1 | 2/2004 | Conti et al. |
| 2004/0068322 A1 | 4/2004 | Ferree |
| 2004/0167631 A1 | 8/2004 | Luchesi et al. |
| 2004/0186585 A1 | 9/2004 | Feiwell |
| 2004/0216259 A1 | 11/2004 | Ponziani |
| 2004/0236431 A1 | 11/2004 | Sekel |
| 2005/0004676 A1 | 1/2005 | Schon et al. |
| 2005/0165408 A1 | 7/2005 | Puno et al. |
| 2005/0192674 A1 | 9/2005 | Ferree |
| 2006/0009857 A1 | 1/2006 | Gibbs et al. |
| 2006/0020345 A1 | 1/2006 | O'Connor et al. |
| 2006/0036257 A1 | 2/2006 | Steffensmeier |
| 2006/0116679 A1 | 6/2006 | Lutz et al. |
| 2006/0142870 A1 | 6/2006 | Robinson et al. |
| 2006/0184173 A1 * | 8/2006 | Collazo ............ A61B 17/155 606/62 |
| 2006/0235541 A1 | 10/2006 | Hodorek |
| 2006/0247788 A1 | 11/2006 | Ross |
| 2007/0038303 A1 | 2/2007 | Myerson et al. |
| 2007/0100346 A1 | 5/2007 | Wyss et al. |
| 2007/0112431 A1 | 5/2007 | Kofoed |
| 2007/0162025 A1 | 7/2007 | Tornier et al. |
| 2007/0173944 A1 | 7/2007 | Keller et al. |
| 2007/0233129 A1 | 10/2007 | Bertagnoli et al. |
| 2007/0276400 A1 | 11/2007 | Moore et al. |
| 2008/0015602 A1 | 1/2008 | Axelson |
| 2008/0097617 A1 | 4/2008 | Fellinger et al. |
| 2008/0103603 A1 | 5/2008 | Hintermann |
| 2008/0109081 A1 | 5/2008 | Bao et al. |
| 2008/0195233 A1 | 8/2008 | Ferrari et al. |
| 2008/0215156 A1 | 9/2008 | Duggal et al. |
| 2008/0287954 A1 | 11/2008 | Kunz et al. |
| 2008/0312745 A1 | 12/2008 | Keller et al. |
| 2009/0054992 A1 | 2/2009 | Landes et al. |
| 2009/0082875 A1 | 3/2009 | Long |
| 2009/0105767 A1 | 4/2009 | Reiley |
| 2009/0105840 A1 | 4/2009 | Reiley |
| 2009/0182433 A1 | 7/2009 | Reiley |
| 2009/0198341 A1 | 8/2009 | Choi et al. |
| 2009/0234360 A1 | 9/2009 | Alexander |
| 2009/0276052 A1 | 11/2009 | Regala et al. |
| 2010/0010493 A1 | 1/2010 | Dower |
| 2010/0023066 A1 | 1/2010 | Long et al. |
| 2010/0023126 A1 | 1/2010 | Grotz |

(56) References Cited

U.S. PATENT DOCUMENTS

| | | |
|---|---|---|
| 2010/0057216 A1 | 3/2010 | Gannoe et al. |
| 2010/0069910 A1 | 3/2010 | Hasselman |
| 2010/0198355 A1 | 8/2010 | Kofoed et al. |
| 2010/0241237 A1 | 9/2010 | Pappas |
| 2010/0305572 A1 | 12/2010 | Saltzman et al. |
| 2010/0318088 A1 | 12/2010 | Warne et al. |
| 2010/0331984 A1 | 12/2010 | Barsoum et al. |
| 2011/0029090 A1 | 2/2011 | Zannis et al. |
| 2011/0035018 A1 | 2/2011 | Deffenbaugh et al. |
| 2011/0035019 A1 | 2/2011 | Goswami et al. |
| 2011/0106268 A1 | 5/2011 | Deffenbaugh et al. |
| 2011/0125200 A1 | 5/2011 | Hanson et al. |
| 2011/0125275 A1 | 5/2011 | Lipman et al. |
| 2011/0125284 A1 | 5/2011 | Gabbrielli et al. |
| 2011/0152868 A1 | 6/2011 | Kourtis et al. |
| 2011/0152869 A1 | 6/2011 | Ek et al. |
| 2011/0166608 A1 | 7/2011 | Duggal et al. |
| 2011/0190829 A1 | 8/2011 | Duggal et al. |
| 2011/0218542 A1 | 9/2011 | Lian |
| 2011/0253151 A1 | 10/2011 | Tochigi et al. |
| 2011/0276052 A1 | 11/2011 | Hasselman |
| 2011/0295380 A1 | 12/2011 | Long |
| 2012/0010718 A1 | 1/2012 | Still |
| 2012/0046753 A1 | 2/2012 | Cook et al. |
| 2012/0053644 A1 | 3/2012 | Landry et al. |
| 2012/0083789 A1 | 4/2012 | Blakemore et al. |
| 2012/0109131 A1 | 5/2012 | Vasarhelyi et al. |
| 2012/0109326 A1 | 5/2012 | Perler |
| 2012/0130376 A1 | 5/2012 | Loring et al. |
| 2012/0136443 A1 | 5/2012 | Wenzel |
| 2012/0185057 A1 | 7/2012 | Abidi et al. |
| 2012/0191210 A1 | 7/2012 | Ratron et al. |
| 2012/0239045 A1 | 9/2012 | Li |
| 2012/0245701 A1 | 9/2012 | Zak et al. |
| 2012/0271430 A1 | 10/2012 | Arnett et al. |
| 2012/0277745 A1 | 11/2012 | Lizee |
| 2013/0041473 A1 | 2/2013 | Rouyer et al. |
| 2013/0116797 A1 | 5/2013 | Coulange et al. |

FOREIGN PATENT DOCUMENTS

| | | |
|---|---|---|
| JP | 2007-518453 A | 7/2007 |
| JP | 2007-519477 A | 7/2007 |
| JP | 4758912 B2 | 6/2011 |
| JP | 5026651 B2 | 6/2012 |
| JP | 2014-131738 A | 7/2014 |
| WO | 01/66021 A1 | 9/2001 |
| WO | 2001066022 A1 | 9/2001 |
| WO | 2005/011523 A2 | 2/2005 |
| WO | 2005072662 A1 | 8/2005 |
| WO | 2006/023824 A2 | 3/2006 |
| WO | 2006/099270 A2 | 9/2006 |
| WO | 2007/084846 | 7/2007 |
| WO | 2009/158522 | 12/2009 |
| WO | 11/151657 | 12/2011 |

OTHER PUBLICATIONS

International Search Report for PCT/US2014/027448 dated Jul. 7, 2014.
Patent Examination Report No. 1 issued in connection with Australian patent application No. 2015202080, Jul. 5, 2016, 4 pages.
Partial European Search Report issued in connection with European patent application No. 14768333.8, Oct. 26, 2016, 6 pages.
Extended European Search Report and Opinion issued in connection with European patent application No. 14768333.8, Jan. 30, 2017, 10 pages.
First Office Action issued for corresponding Japanese patent application No. 2016-117842, Sep. 12, 2017, 5 pages.
Second Office Action issued in connection with corresponding Chinese Patent Application No. 20180027987.4, Jul. 16, 2018, 6 pages.
Notice of Grant issued in connection with corresponding Japanese Patent Application No. 2016-502443, Aug. 28, 2018, 3 pages.
Extended European Search Report and Written Opinion issued in connection with European Patent Application No. 18160378.8, Jun. 29, 2018, 7 pages.

\* cited by examiner

ALIGNMENT GUIDE, SYSTEMS, AND METHODS

CROSS-REFERENCE TO RELATED APPLICATIONS

This application claims priority to U.S. Provisional Patent Application No. 63/167,926, filed Mar. 30, 2021, the entirety of which is incorporated by reference herein.

FIELD OF DISCLOSURE

The disclosed guides, systems, and methods are directed to surgical implants. More particularly, the disclosed guides, systems, and methods are directed to providing intraoperative alignment for one or more cutting guides.

BACKGROUND

Joint replacement surgeries seek to replace the joint of a patient such that the joint functions as well as a native joint. Various guides typically are used in performing these surgeries, including guides for resecting one or more bones comprising the joint as well as ensuring the proper alignment and placement of the prosthesis. For example, these guides may provide a surgeon with the ability to visualize and/or approximate a mechanical axis of one or more bones of the patient.

SUMMARY

In some embodiments, an alignment guide includes a base, a swing arm for coupling to the base such that the swing arm is movable relative to the base, and a locking device for selectively fixing a position of the swing arm relative to the base. The base defines at least one first hole sized and configured to receive a first fixation element and defines at least one second hole sized and configured to receive a second fixation element. The swing arm extends from a first end to a second end. The second end of the swing arm including a coupling mechanism for coupling another guide to the second end of the swing arm.

In some embodiments, a method includes positioning an alignment guide relative to a bone, adjusting a position of a swing arm of the alignment guide while a position of a base of the alignment guide remains fixed relative to the bone, fixing the position of the swing arm relative to the base, and coupling a second guide to the alignment guide.

DETAILED DESCRIPTION

This description of the exemplary embodiments is intended to be read in connection with the accompanying drawings, which are to be considered part of the entire written description.

The disclosed guides, systems, and methods provide a surgeon with the ability to confirm and/or adjust the placement of a cutting guide without the need to manually remove one or more pre-placed pins. As such, these guides, systems, and methods advantageously provide the surgeon with flexibility in the operating theater to adjust a position of a cutting guide and to perform such adjustment with precision and accuracy compared to conventional methods of manual and/or unguided adjustment.

Figure 1:
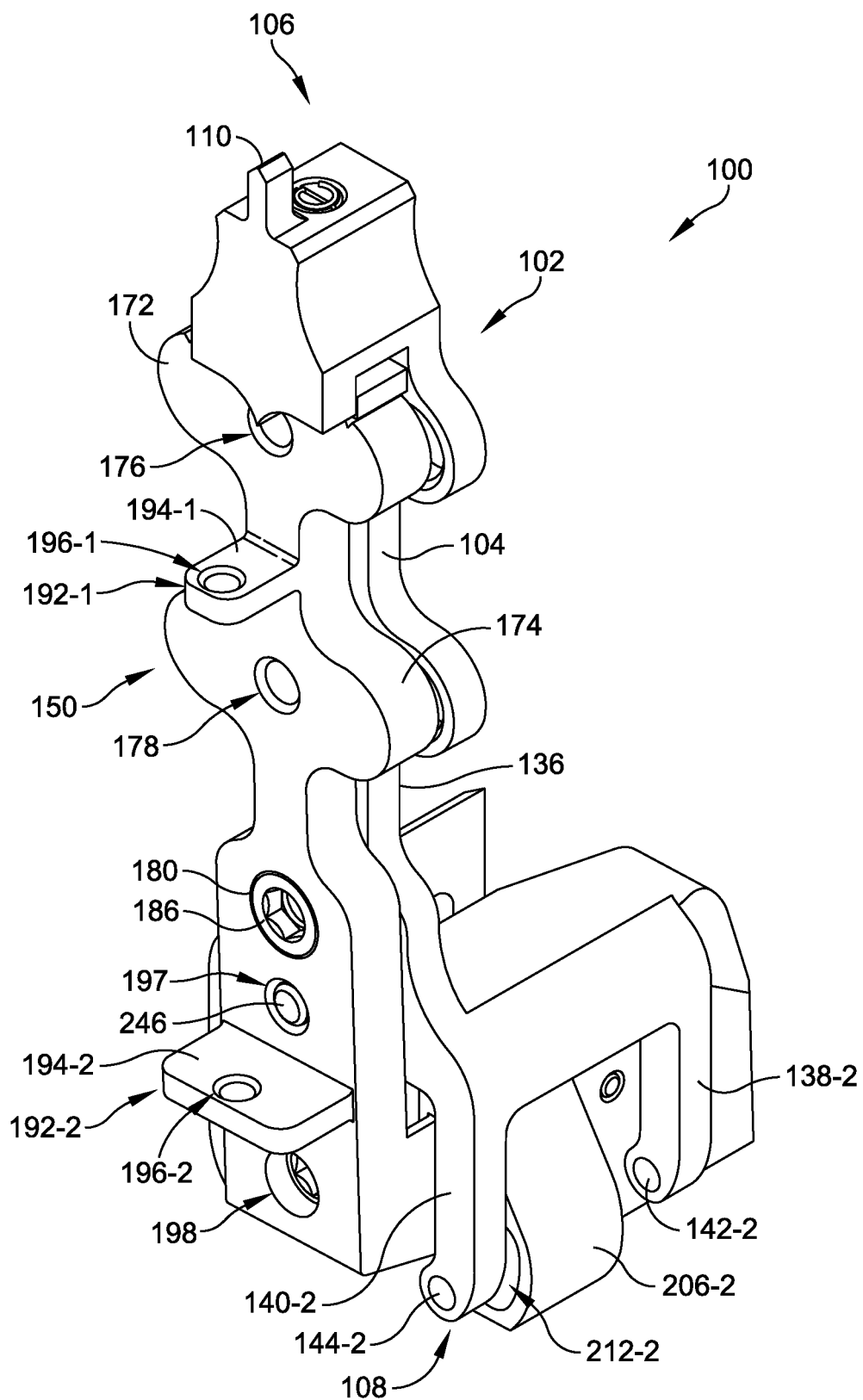
FIG. 1 is a perspective view of one example of an alignment guide in accordance with some embodiments.

FIG. 1 illustrates one example of an alignment guide in accordance with some embodiments. The alignment guide 100 illustrated in FIG. 1 may include a base 102 and swing arm 150 coupled to the base. Base 102 includes a body 104 extending from a first end 106 to a second end 108.

Figure 2:
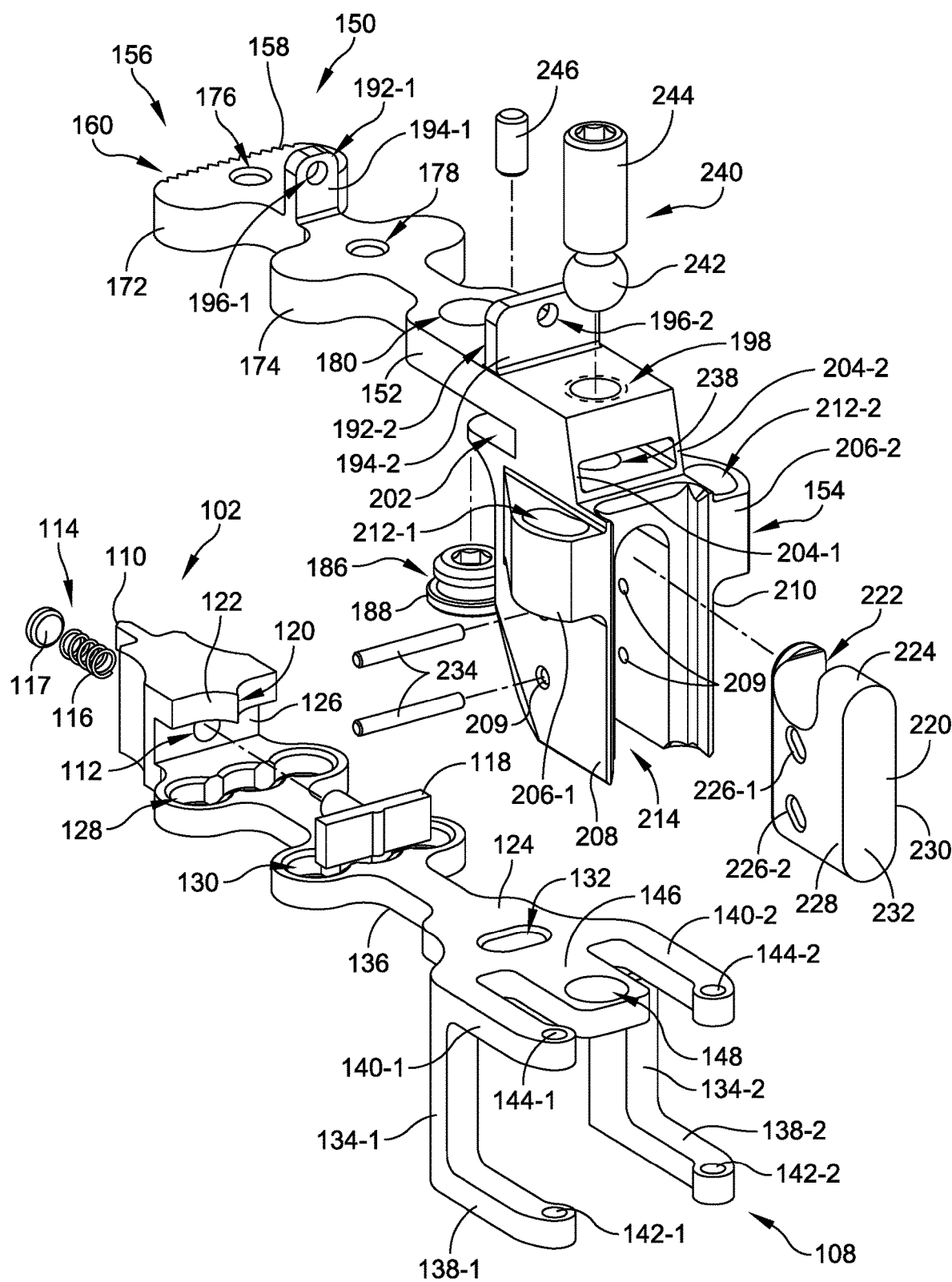
FIG. 2 is an exploded perspective view of the alignment guide illustrated in FIG. 1 in accordance with some embodiments.

In some embodiments, first end 106 may terminate in one or more points 110 or other shape for indicating alignment as will be understood by one of ordinary skill in the art. The first end 106 may define a hole or cavity 112 sized and configured to receive a spring-biased detent 114. As best seen in FIG. 2, spring-biased detent 114 may include a biasing member 116, such as a compression spring, a cap 117, and a detent 118 coupled to the biasing member 116. In some embodiments, the spring-biased detent 114 is configured to provide audible and/or tactile feedback to a user indicating the angular adjustment of the guide 100 as described in greater detail below.

Figure 3:
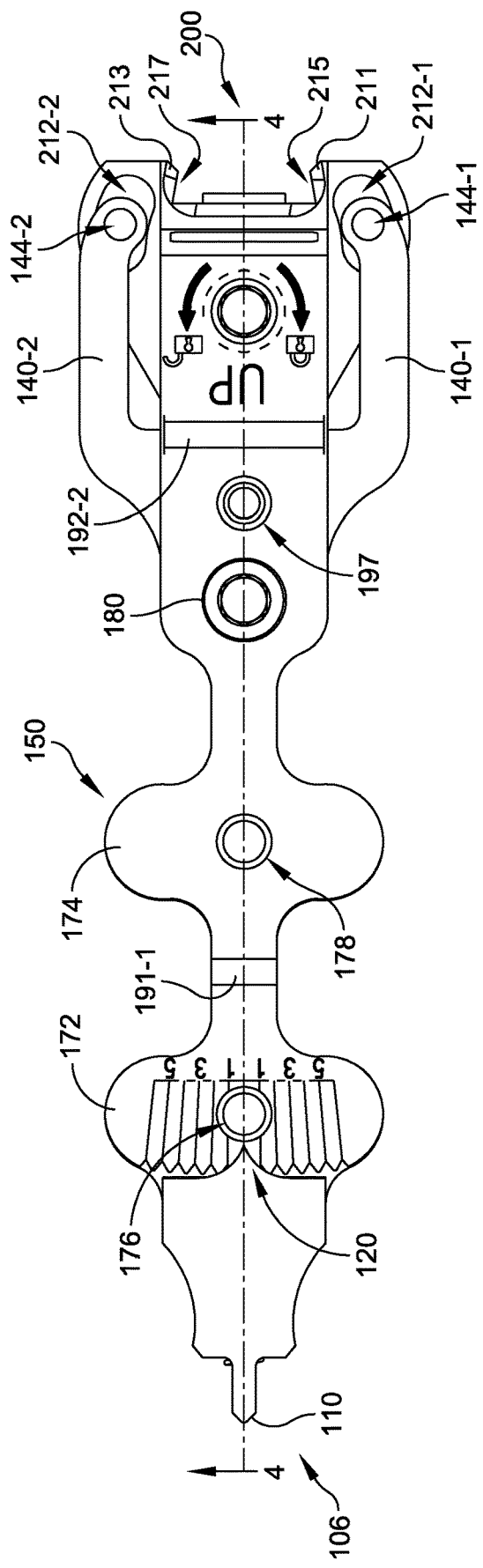
FIG. 3 is a top side plan view of the alignment guide illustrated in FIG. 1 in accordance with some embodiments.

In some embodiments, first end 106 may also include a second point or indicator 120 is collinearly arranged with point 110 but oriented such that indicator 120 is directed in a direction that is opposite to the direction in which point 110 is oriented (FIG. 3). As best seen in FIG. 2 the indicator 120 is positioned on a ledge 122, which is located above a first upper surface 124 of body 104. The hole or cavity 112 extends inwardly from vertical surface 126 and between upper surface 124 and ledge 122.

In some embodiments, body 104 of base 102 defines first and second sets of interconnected holes 128, 130. The first and second sets of interconnected holes 128, 130 may be spaced apart from one another along a length of body 104 as shown in FIG. 2. In some embodiments, the sets of interconnected holes 128, 130 extend entirely through body 104 of base 102. Body 104 may also define a slot 132 along its length. Slot 132 may extend through body 104 and have a length that is oriented perpendicular to a longitudinal axis defined by body 104. In some embodiments, slot 132 does not extend entirely through body 104. As described in greater detail below, slot 132 is sized and configured to receive a dowel pin 246 or other device for constraining the movement of swing arm 150 relative to base 102 as will be understood by one of ordinary skill in the art. In some embodiments, slot 132 is provided between the second set of interconnected holes 130 and the end 108 of body 104. However, one of ordinary skill in the art will understand that slot 132 may be formed at other locations along the length of body 104. Further, slot 132 may be replaced with a hole sized and configured to receive the dowel pin 246, and swing arm 150 may define a corresponding slot.

Second end 108 of base 102 may include one or more extensions 134-1, 134-2 (collectively, "extensions 134") that extend in a downward direction from the lower surface 136 of body 104. Each extension 134-1, 134-2 may include a respective arm 138-1, 138-2 (collectively, "arms 138" or "lower arms 138") that extends from the bottom of each extension as shown in FIG. 2. Second end 108 may also include one or more upper arms 140-1, 140-2 (collectively, "arms 140" or "upper arms 140"). Arm 140-1 extends parallel to lower arm 138-1, and upper arm 140-2 extends parallel to lower arm 138-2. Lower arms 138-1, 138-2 define a respective hole 142-1, 142-2. Upper arms 140-1, 140-2 may also define a respective hole 144-1, 144-2. Hole 142-1 may be aligned with hole 144-1 such that a k-wire or other fixation device may be received within holes 142-1, 144-1, and hole 142-2 may be aligned with hole 144-2 such that a k-wire or other fixation device may be received within holes 142-2, 144-2.

In some embodiments, body 104 includes a projection 146 that extends parallel to upper arms 140. Projection 146 may be located between arms 140 as best seen in FIG. 2. Projection 146 may define a hole 148 sized and configured to allow a locking screw (described in greater detail below) to pass therethrough. As such, in some embodiments, the hole 148 has a diameter that is greater than a diameter of ball 242.

Swing arm 150 may have an elongate body 152 and a housing 154. A first end 156 of body 152 may include a number of teeth 158 arranged along a front edge 160 of end 156. The teeth 158 may be sized and arranged to be engaged by the spring-biased detent 114 supported by base 102.

Figure 6:
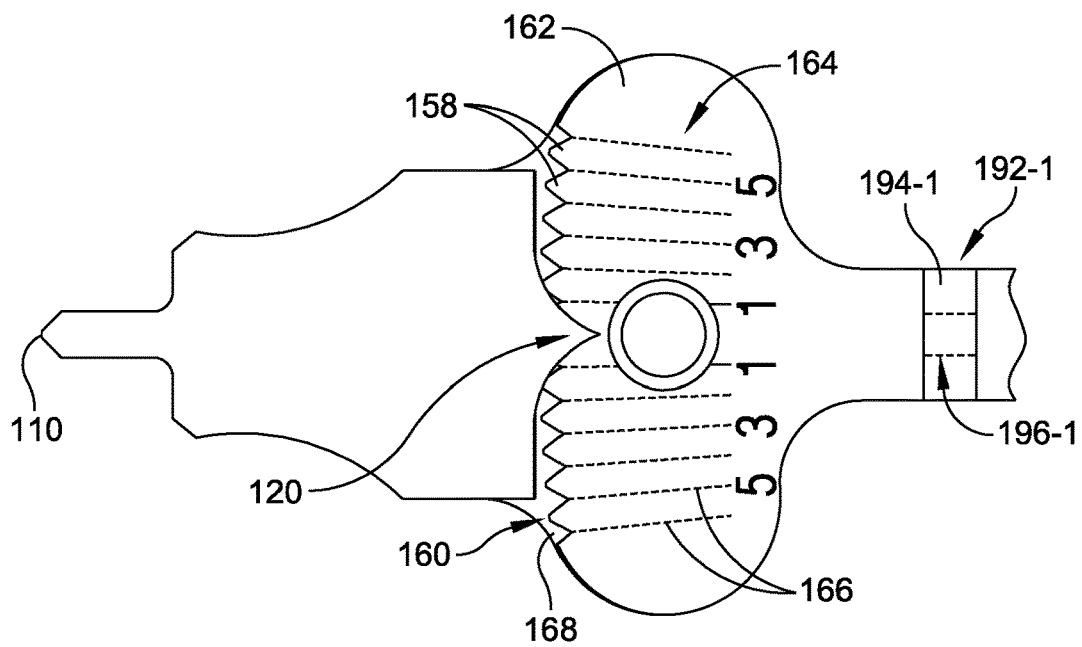
FIG. 6 is a detailed plan view of a first end of the alignment guide illustrated in FIG. 1 in accordance with some embodiments.
Figure 7:
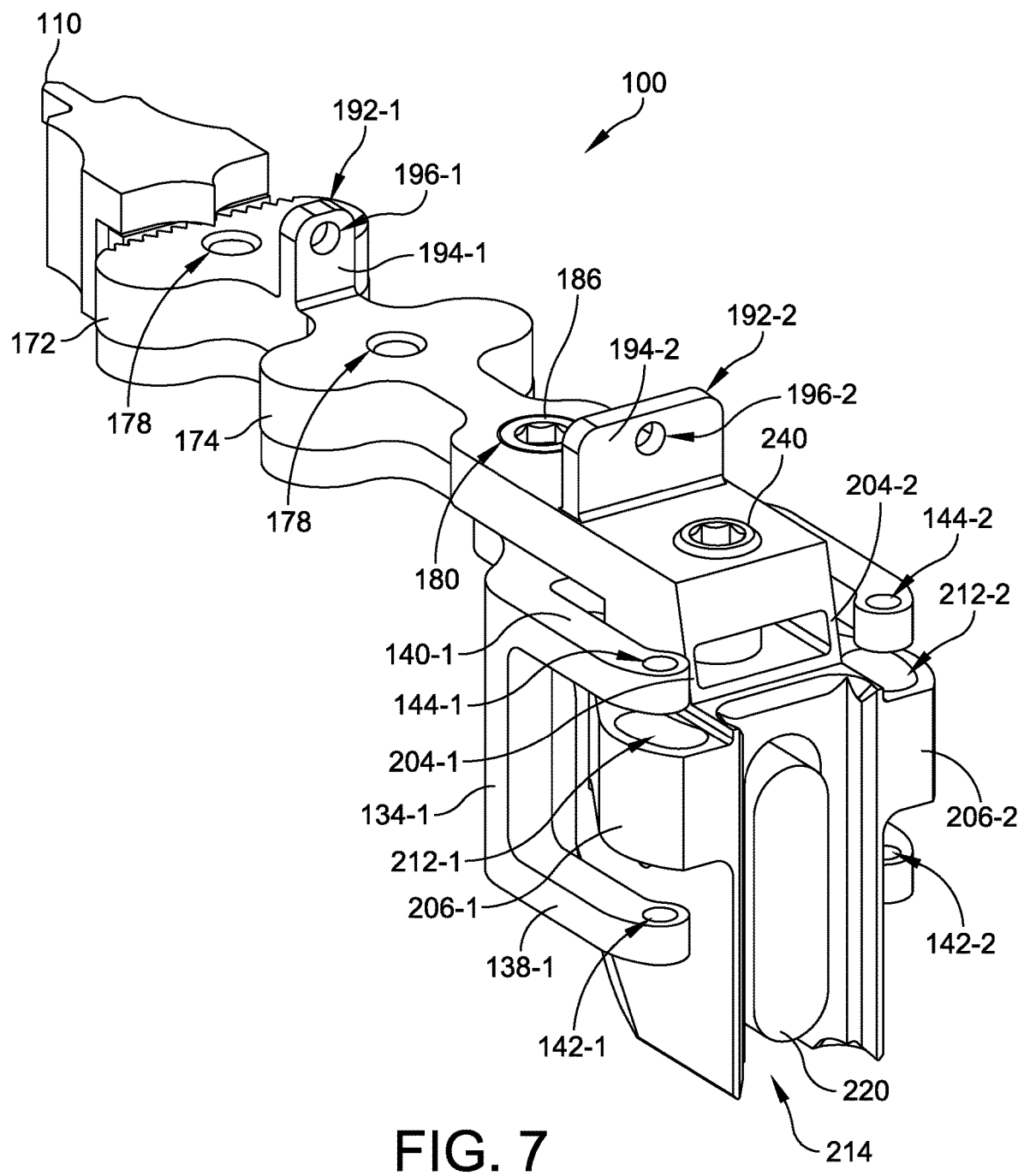
FIG. 7 is another perspective view of the alignment guide illustrated in FIG. 1 in accordance with some embodiments.

In some embodiments, upper surface 162 of end 156 may include indicia 164, which indicate an angle alignment as described in more detail below. As best seen in FIG. 6, the indicia 164 may include a plurality of lines or grooves 166 that extend from a trough 168 formed between adjacent teeth 158. In some embodiments, adjacent troughs 168 are separated by a distance corresponding a specific adjustment angle described in greater detail below. A middle or central trough 170 (not visible in FIG. 6) may be provided that aligns with a central longitudinal axis defined by the body 152 of swing arm 150.

Figure 5:
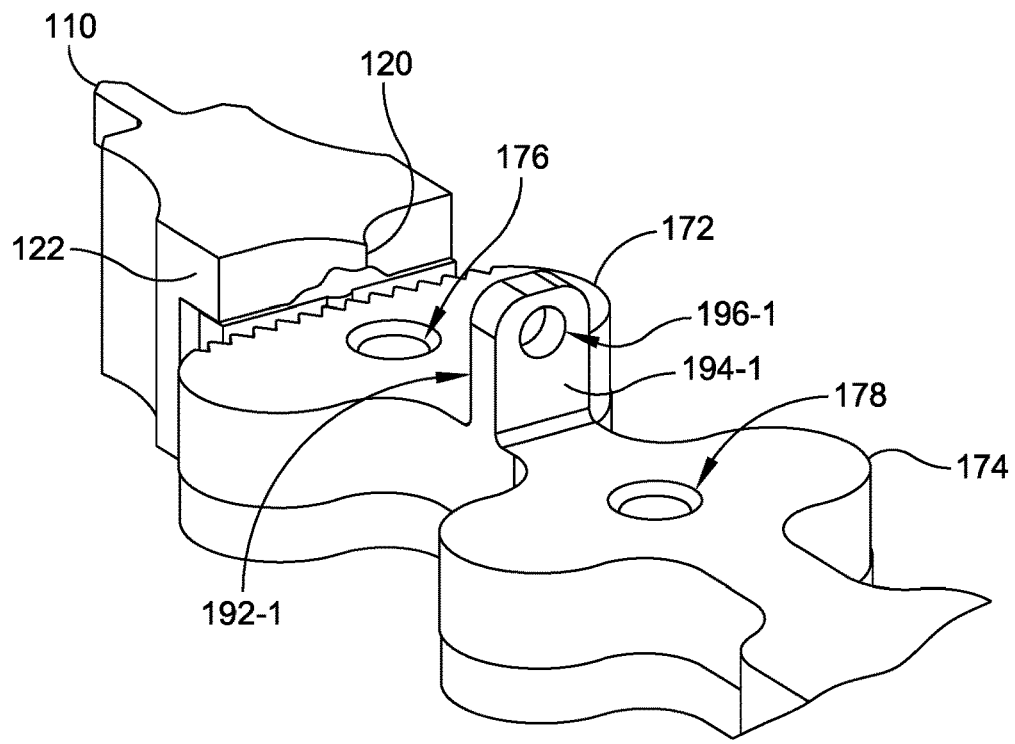
FIG. 5 is a detailed perspective view of a first end of the alignment guide illustrated in FIG. 1 in accordance with some embodiments.

As best seen in FIGS. 2 and 5, body 152 may include one or more oblong sections 172, 174 that are spaced apart from one another along the length of body 152. In some embodiments, oblong sections 172, 174 have an outer contour that is similar to the contour provided by the portions of body 104 defining the sets of interconnected holes 128, 130. More particularly, the outer or peripheral contour of oblong section 172 may align within or be similar in shape to the outer contour or shape of the section of body 104 in which the first set of interconnected holes 128 is provided, and the outer or peripheral contour of oblong section 174 may align with or be similar in shape to the outer contour or shape of the section of body 104 in which the second set of interconnected holes 130 is provided.

Further, in some embodiments, a hole 176 is provided along oblong section 172 and a hole 178 is provided along oblong section 174. Hole 176 is arranged such that it may be aligned with one of the holes of the first set of interconnected holes 128, and hole 178 is arranged such that it may be aligned with one of the holes of the second set of interconnected holes 130.

Figure 4:
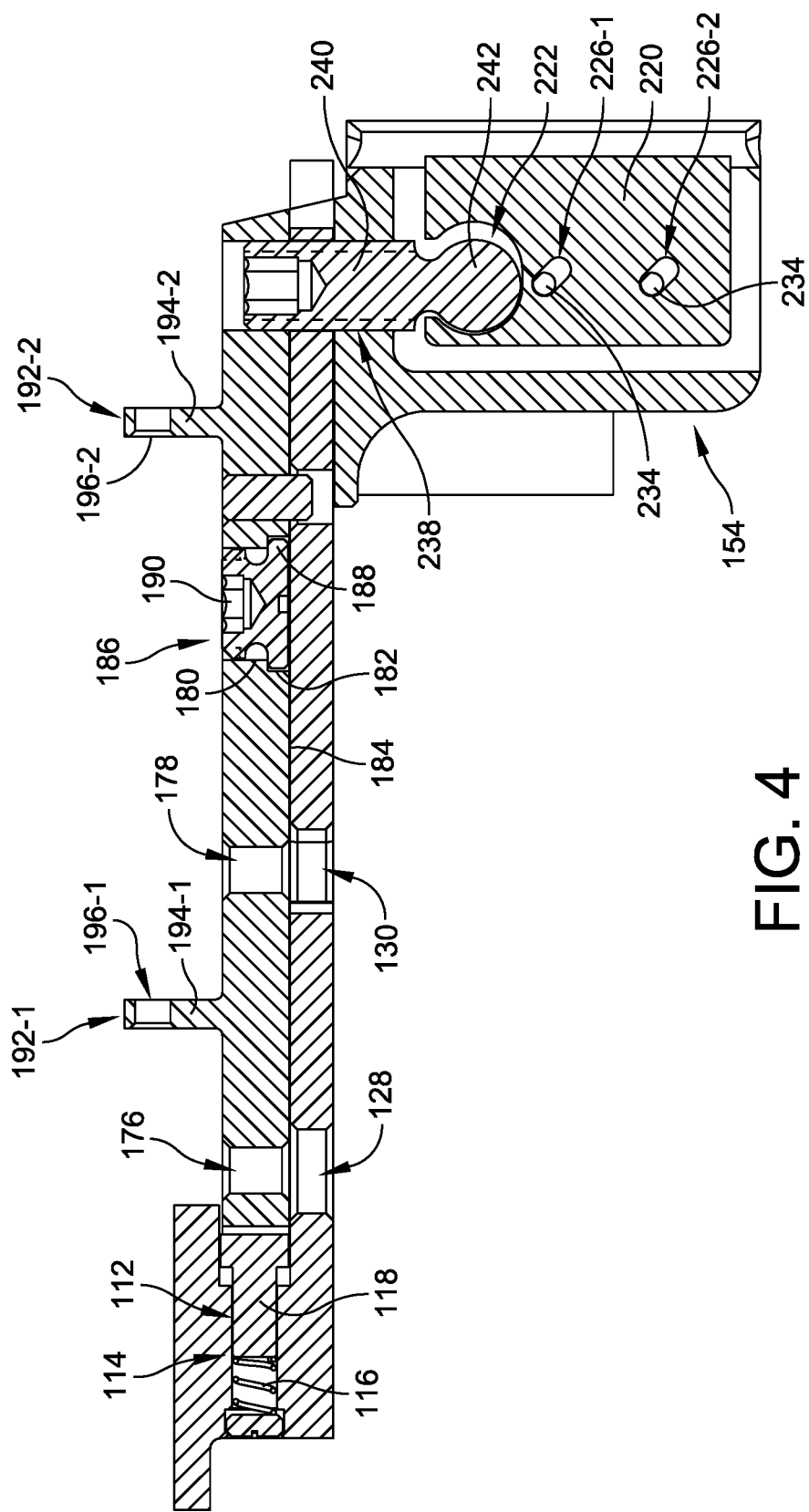
FIG. 4 is a sectional view of the alignment guide illustrated in FIG. 1 taken along line 4-4 in FIG. 3 in accordance with some embodiments.

Body 152 defines another hole 180, which may be positioned along the central longitudinal axis defined by the body 152. Hole 180 may be partially or fully threaded and include a countersink or undercut section 182, which may inwardly extend from the lower planar surface 184 of body 152 as best seen in FIG. 4. Hole 180 is sized and configured to receive a locking screw 186 therein. As best seen in FIGS. 2 and 4, locking screw 186 may include an outwardly extending flange 188, which may have a diameter that may be greater than a diameter of the rest of the locking screw 186, and an engagement feature 190 at an end disposed opposite of the flange 188. Flange 188 is sized and configured to be received within countersink or undercut section 182 of hole 180.

In some embodiments, the upper surface 162 of body 152 may include one or more pin holders 192-1, 192-2 (collectively, "pin holders 192"). Each pin holder 192-1, 192-2 may include a respective projection 194-1, 194-2 (collectively, "projections 194") each defining a respective hole 196-1, 196-2 (collectively, "holes 196"). Holes 196 may be sized and configured to receive a k-wire, pin, or other elongate object therein and are arranged such that when the k-wire, pin, or elongate object may be received within the holes 196, the k-wire, pin, or other elongate object extends along a central longitudinal axis defined by swing arm 150. The k-wire, pin, or other elongate object may enhance the visualization for the user to check the alignment of the swing arm 150 relative to a mechanical axis of the patient.

Body 152 may also define a hole 197, which may be sized and configured to receive dowel 246, and a hole 198, which may be at least partially threaded. In some embodiments, hole 198 is positioned between pin holder 192-2 and end 200 of body 152. Hole 198 may be positioned such that it will be aligned with hole 148 when the swing arm 150 is coupled to the base 102 and may be dimensioned to receive and engage locking screw 240 as described in greater detail below.

Housing 154 may extend from lower surface 184 of body 152. In some embodiments, a gap 202 is provided between the lower surface 184 of body 152 and housing 154 such that housing 154 is coupled to body 152 by one or more appendages 204-1, 204-2 (collectively, "appendages 204"). Gap 202 may be dimensioned to receive projection 146 of base 102 in sliding engagement. In some embodiments, housing 154 includes first and second wings 206-1, 206-2 (collectively, "wings 206") extending outwardly from opposite sides 208, 210 of housing 154. Each wing 206-1, 206-2 may define a respective slot 212-1, 212-2 (collectively, "slots 212") that are positioned on housing 154 such that the slots 212 are aligned with holes 142, 144 when the swing arm 150 is coupled to base 102. More particularly, slot 212-1 may be aligned with holes 142-1, 144-1 when swing arm 150 is coupled to base 102, and slot 212-2 may be aligned with holes 142-2, 144-2 when swing arm 150 is coupled to base 102. Slots 212 may be sized and configured to receive a k-wire, pin, or other fixation device therein while permitting the swing arm 150 to move relative to the k-wires, pins, or other fixation devices as described in greater detail below.

Housing 154 may define a chamber 214 sized and configured to receive a locking block 220. In some embodiments, chamber 214 extends inwardly between side 210 and side 208 of housing 154 and is in communication with hole 238. Hole 238 may be aligned with hole 198 defined by body 152 of swing arm 150 and be sized and configured to provide clearance for receiving locking screw 240.

Locking block 220 may define a contoured (e.g., an oblong sphere) cavity 222 extending inwardly from side 224. Cavity 222 may be contoured to facilitate engagement between locking block 220 and the ball 242 of locking screw 240, which may be a ball head screw as shown in FIG. 2, including a ball 242 coupled to a shaft 244. Locking block 220 may include one or more slots 226-1, 226-2 (collectively, "slots 226") that extend from side 228 to side 230 of locking block 220. In some embodiment, slots 226 are formed such that a length of the slots 226 is angled with respect to a planar surface provided by side 232, which extends between sides 228, 230 and is disposed adjacent to side 224. Slots 226 may be sized and configured to receive dowel pins 234 or other coupling elements for coupling locking block 220 to housing 154. For example, dowel pins 234 may be received within slots 226 of locking block 220 and holes 209 defined by the sides 208, 210 of housing 154. The combination of slots 226, holes 209, and cavity 222 may enable locking block 220 to move relative to housing 154 and facilitate locking of a cutting guide to the guide 100 as described below.

Housing 154 may include a pair of spaced apart rails 211, 213 each defining an respective undercut 215, 217 for forming a dovetail connection with a cutting guide, such as with the dovetail extension 394 of coronal sizing and drill guide 380 described in U.S. Pat. No. 10,136,904, entitled "ANKLE REPLACEMENT SYSTEM AND METHOD" (the "'904 patent"), the entirety of which is incorporated by reference herein. A person of ordinary skill in the art will understand that housing 154 may include connection mechanisms other than a dovetail connection for coupling the guide 100 to one or more sizing and/or cutting guides.

Swing arm 150 may be coupled to base 102 by sliding projection 146 of base 102 into gap 202. When projection 146 is received within gap 202, lower arms 138 and upper arms 140 at least partially surround housing 154 of swing arm 150 such that holes 142, 144 defined by arms 138, 140 are aligned with slots 212 defined by wings 206. Dowel pin 246 is inserted into hole 197 defined by swing arm 150 and into slot 132 defined by base 102. The locking screw 240 is received within cavity 222 defined by locking block 220 and inserted into holes 198, 238. Locking block 220 is pinned to swing arm 150 by inserting pins 234 into holes 209 defined by the body 152 of swing arm 150 that are also received within slots 226 defined by locking block 220.

Figure 8:
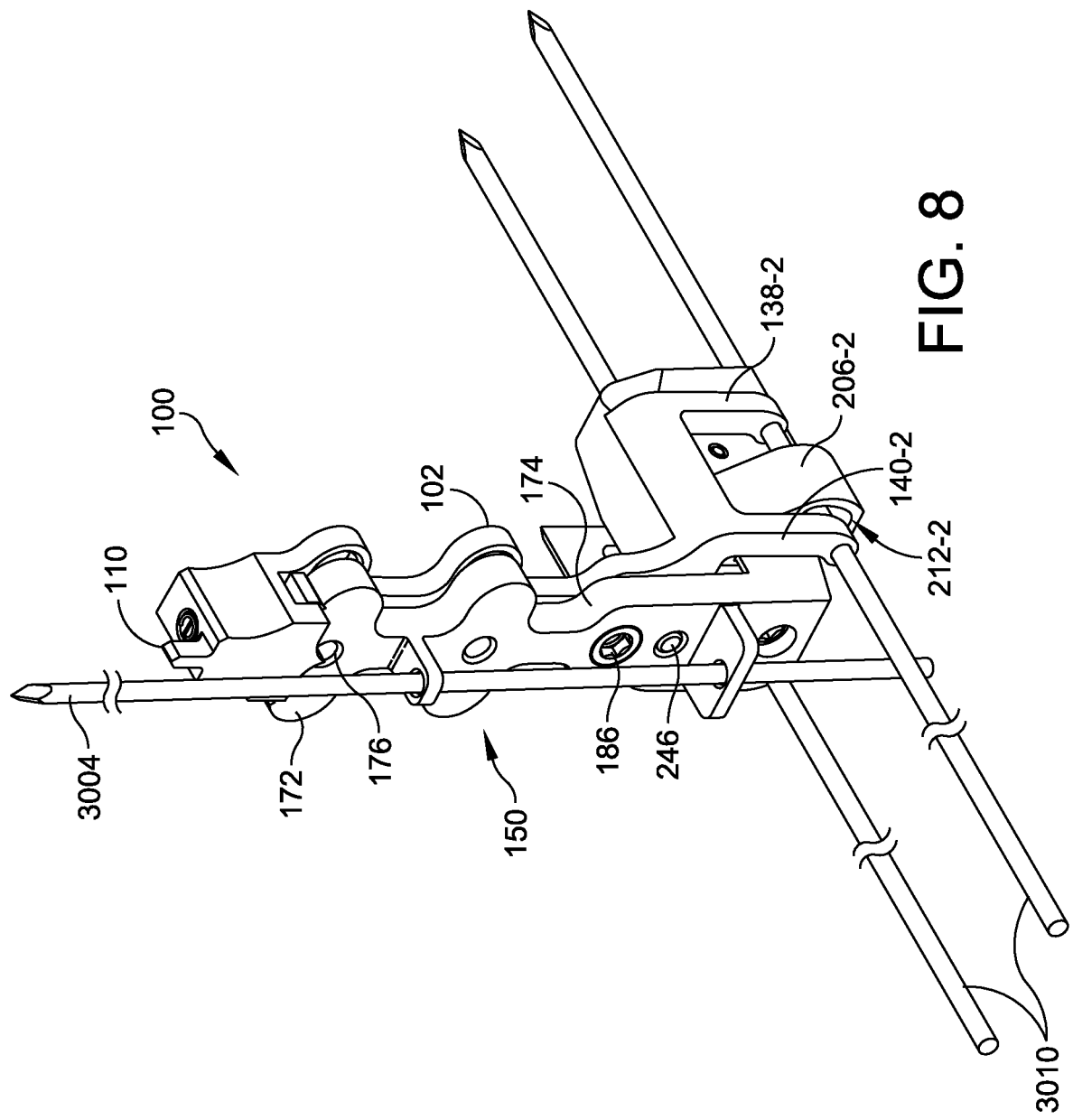
FIG. 8 is a perspective view of pins being inserted through the alignment guide illustrated in FIG. 1 in accordance with some embodiments.

In use, a surgeon or other individual may place one or more pins or k-wires (e.g., a 2.4 mm Steinmann pin) in the anterior surface of a patient's tibia based on the use of a patient-specific mount, such as patient-specific mount 3000 and pins 3010 described in the '904 patent. With pins inserted in the patient, the patient-specific mount 3000 is removed from its engagement with the pins and the alignment guide 100 is then placed over the pins 3010. More particularly, the pins 3010 are received within holes 142, 144 defined by arms 138, 140 and within slots 212 as best seen in FIG. 8.

With alignment device 100 coupled to pins 3010, a surgeon or other individual may check to confirm a cutting guide will be properly oriented and/or adjust the alignment of a cutting guide without having to remove pins 3010. For example, varus/valgus adjustment may be made by rotating swing arm 150 relative to base 102. As noted above, the swing arm 150 is able to rotate relative to base 102 about an axis defined by holes 148, 198, 238 in which locking screw 240 is received. Rotation and relative movement between swing arm 150 and base 102 is permitted by slots 132, 212.

As swing arm 150 moves relative to base 102, detent 118 provides audible and/or tactile feedback as it engages the teeth 158 (and the troughs 168 between teeth 158). Further, indicia 164, if provided, indicate the amount of varus/valgus adjustment (e.g., 1°, 2°, etc.) based on movement of the swing arm 150. When the desired adjustment has been achieved, the position of swing arm 150 to base 102 may be fixed using locking screw 186. Rotation of screw 186 in a first direction (e.g., clockwise direction) may lock the position of swing arm 150 to base 102, and rotation of screw 186 in a second direction (e.g., counter-clockwise direction) may permit relative movement of swing arm 150 to base 102.

It should be appreciated that a guide, such as a coronal sizing and drill guide 380 or cutting guide as described in the '904 patent, may be coupled to alignment guide 100 prior to or after the angular adjustment is performed. Such a guide may be coupled to alignment guide 100 by inserting a dovetail extension into the corresponding dovetail/undercuts 215, 217 provided by rails 211, 213 of housing 154. The cutting or drill guide may be locked to the housing 154 by rotating locking screw 240 in a first direction (e.g., counter-clockwise) as shown in FIG. 3. Unlocking is provided by the ball head 242 engaging the surface(s) defining cavity 222 of locking block 220, which causes locking block 220 to be pulled inwardly into chamber 214 guided by the engagement of pins 234 and slots 226 decoupling alignment guide 100 from the cutting and/or drill guide. Rotating the locking screw 240 in a second, opposite direction (e.g., clockwise) results in the locking of the cutting and/or drill guide from alignment guide 100, as also indicated in FIG. 3, such that the alignment guide 100 may be coupled to the cutting and/or drill guide. For example, the dovetail connection between the alignment guide 100 and the cutting and/or drill guide may be engaged by sliding the alignment guide 100 relative to the cutting and/or drill guide.

If desired, an elongate radiopaque member, such as a k-wire or pin, may be inserted through holes 196 defined by pin holders 192 to provide for a fluoroscopic check. For example, FIG. 8 illustrates a radiopaque member 3004 being positioned within holes 196 defined by the pin holders 192 such that the radiopaque member 3004 extends parallel to a longitudinal axis defined by the swing arm 150. Under fluoroscopy, a surgeon or other individual may check to determine whether the radiopaque member 3004 is aligned with a mechanical and/or longitudinal axis defined by a bone, such as the tibia, of the patient. A person of ordinary skill in the art will understand that the fluoroscopic check may be performed before or after the cutting and/or drill guide is coupled to the alignment guide 100.

Figure 9:
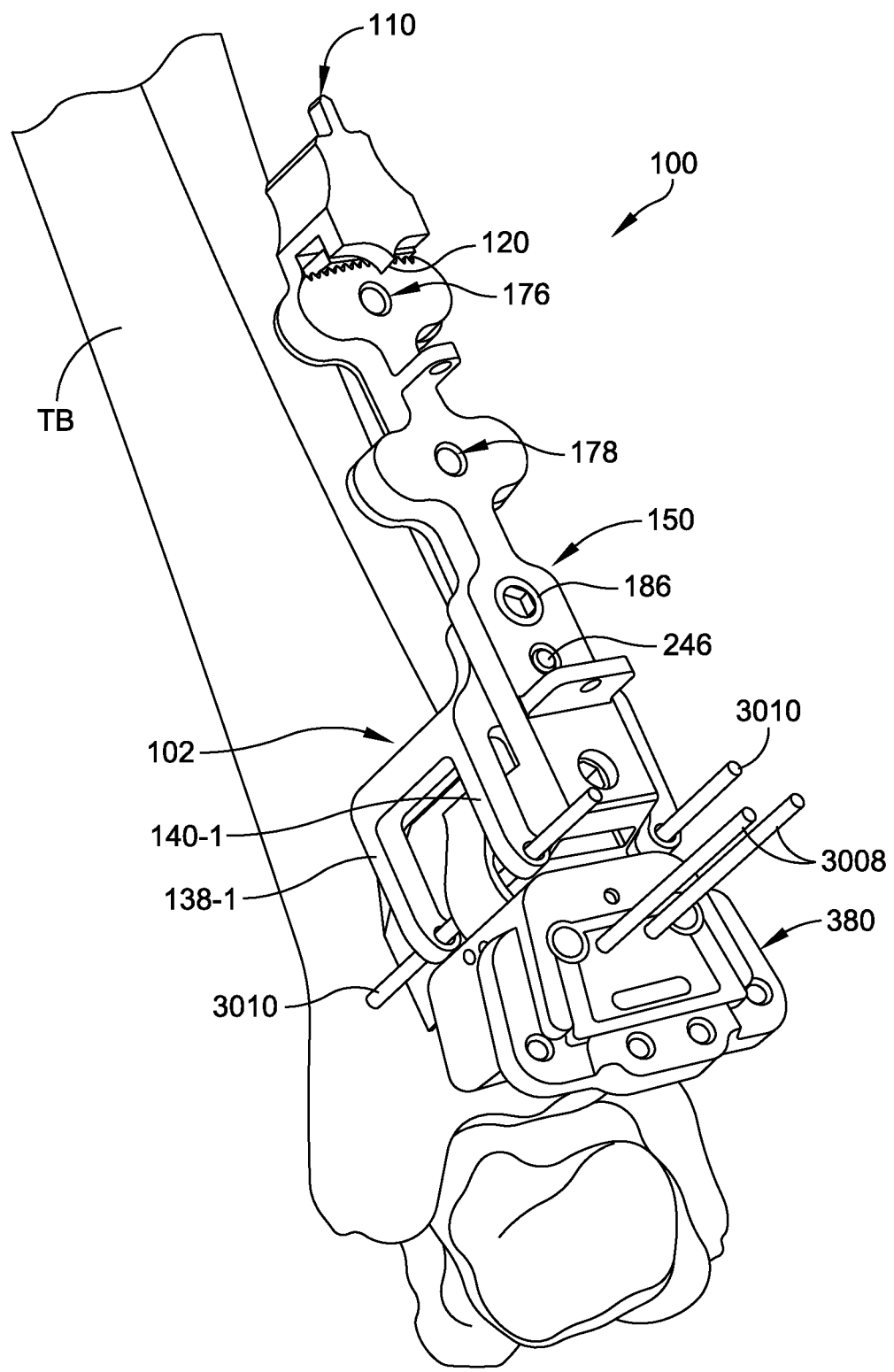
FIG. 9 illustrates the alignment guide illustrated in FIG. 1 coupled to a bone and to another guide in accordance with some embodiments.

FIG. 9 shows alignment guide 100 coupled to a distal portion of a bone, which in this example is a distal portion of a tibia TB. As shown in FIG. 9, the alignment guide is coupled to the bone TB via pins 3010, which are received within holes 142, 144 defined by arms 138, 140 of base 102 and within slots 212 defined by the wings 206 of swing arm 150. A coronal sizing and drill guide 380 (as described in the '904 patent) is shown as coupled to alignment guide 100. Pins 3008 may be used to secure the guide 380 to bone.

Figure 10:
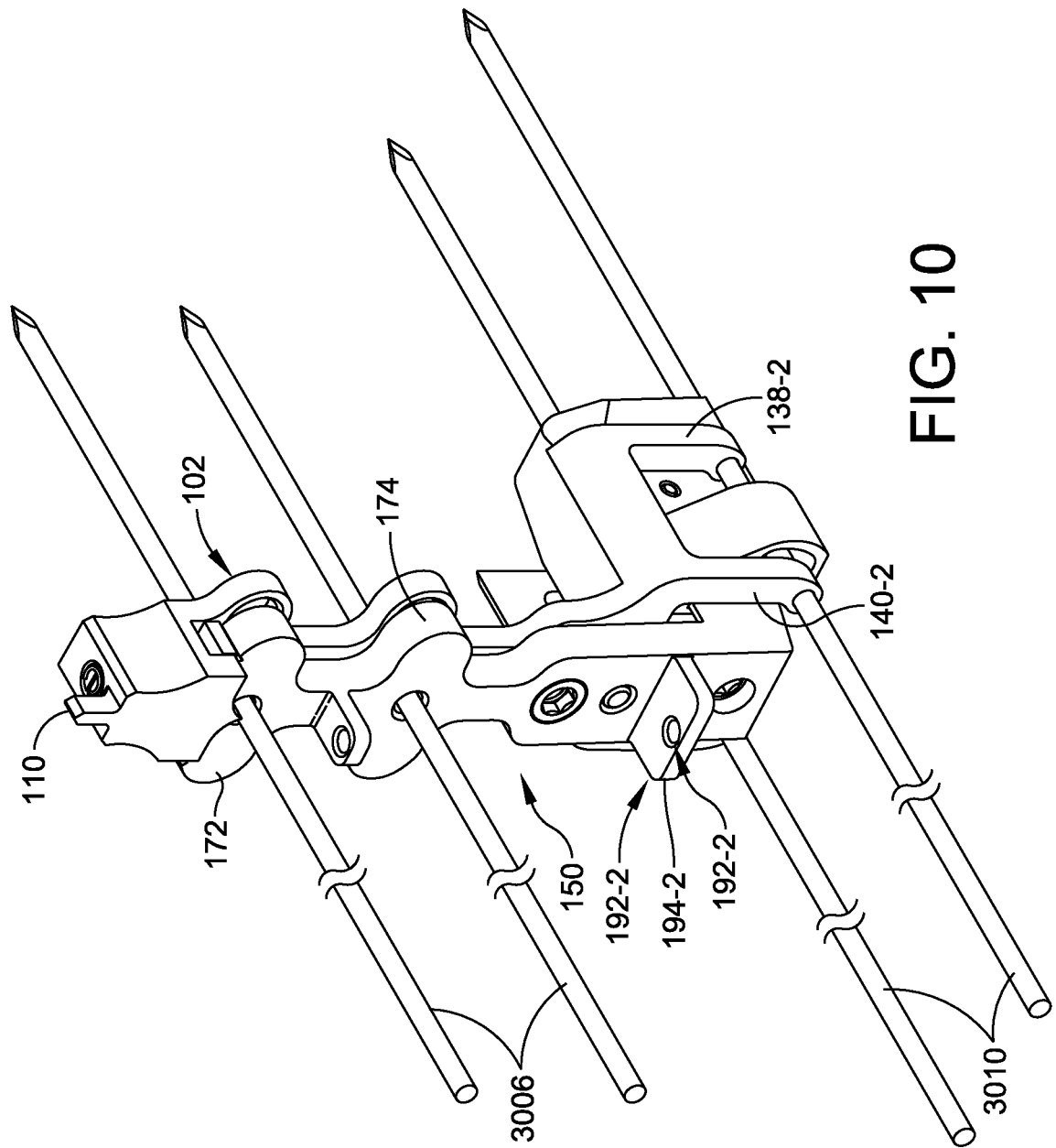
FIG. 10 is another perspective view of pins being inserted through the alignment guide illustrated in FIG. 1 in accordance with some embodiments.
Figure 11:
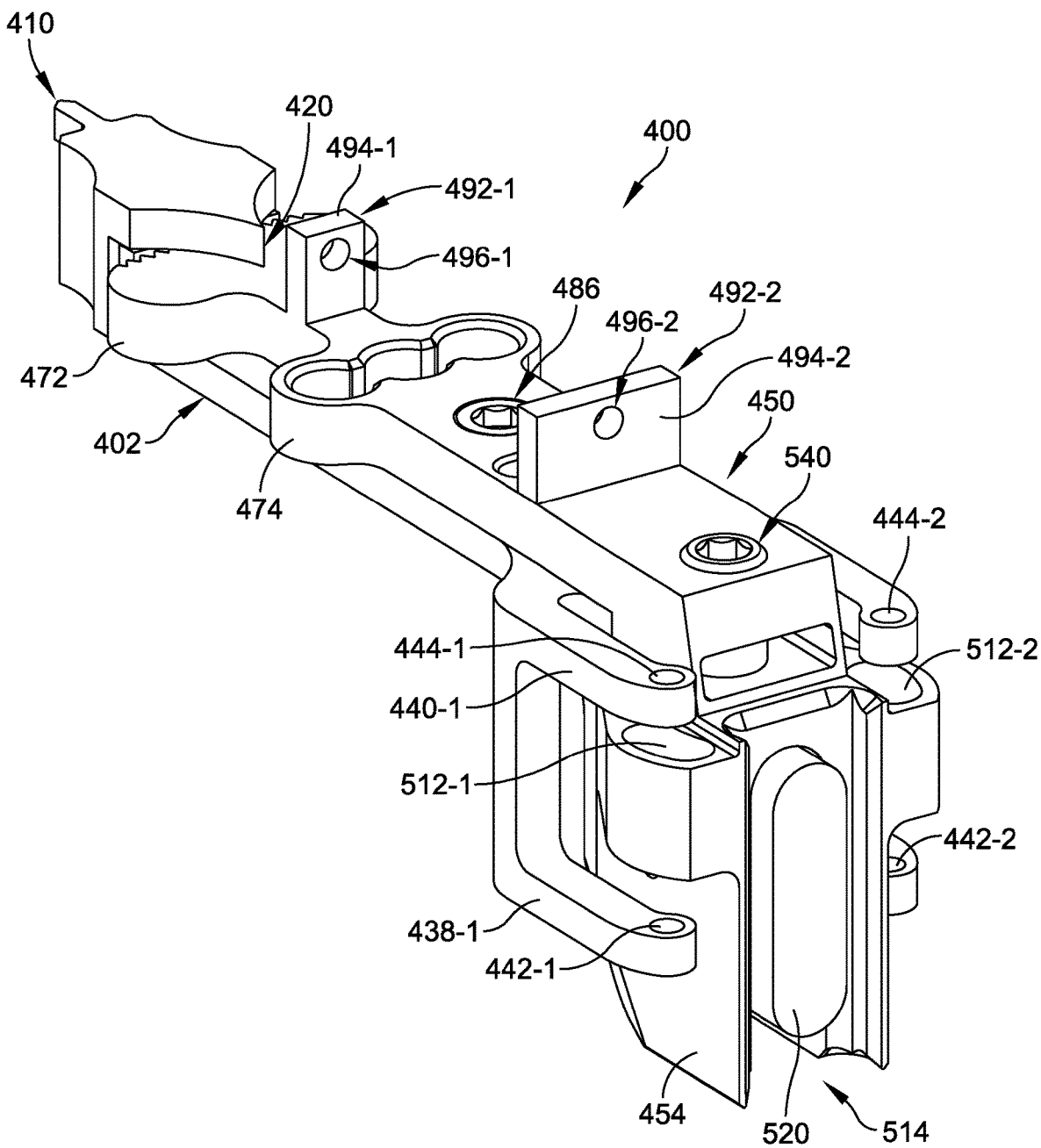
FIG. 11 is a perspective view of another example of an alignment guide in accordance with some embodiments.

The holes 176, 178 defined by swing arm 150 provide the surgeon with the ability to form holes in a patient's bone that facilitate the use of additional instruments. For example, as shown in FIG. 10, pins 3006, which can be the same type and size (e.g., 2.4 mm Steinmann) or a different type or size as pins 3010, may be inserted through holes 176, 178, which are aligned respectively with interconnected holes sets 128, 130 defined by base 102. Once pins 3006 have been inserted, additional instrumentation, such as an adjustment block 100 and/or an alignment frame subassembly 105 described in the '904 patent, may be coupled to the pins 3006.

It should be appreciated, however, that the alignment guide may take other forms or configurations. Another example of an alignment guide 400 is shown in FIGS. 11-14. Features of alignment guide 400 that are common to those of alignment guide 100 have the same reference numeral incremented by 300. Repetitive descriptions of common elements of alignment guides 100, 400 are not provided herein.

Figure 12:
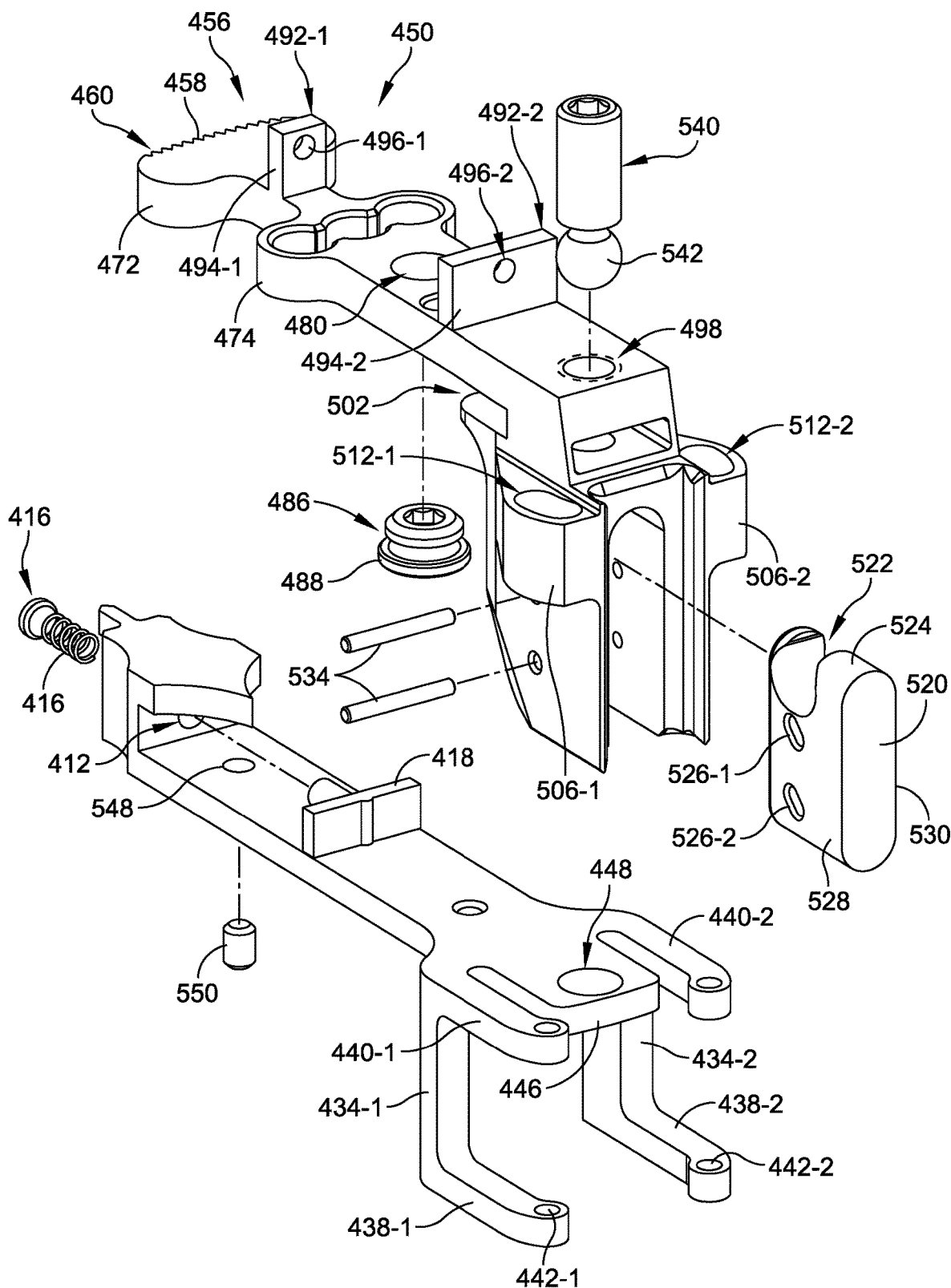
FIG. 12 is an exploded perspective view of the alignment guide illustrated in FIG. 11 in accordance with some embodiments.
Figure 14:
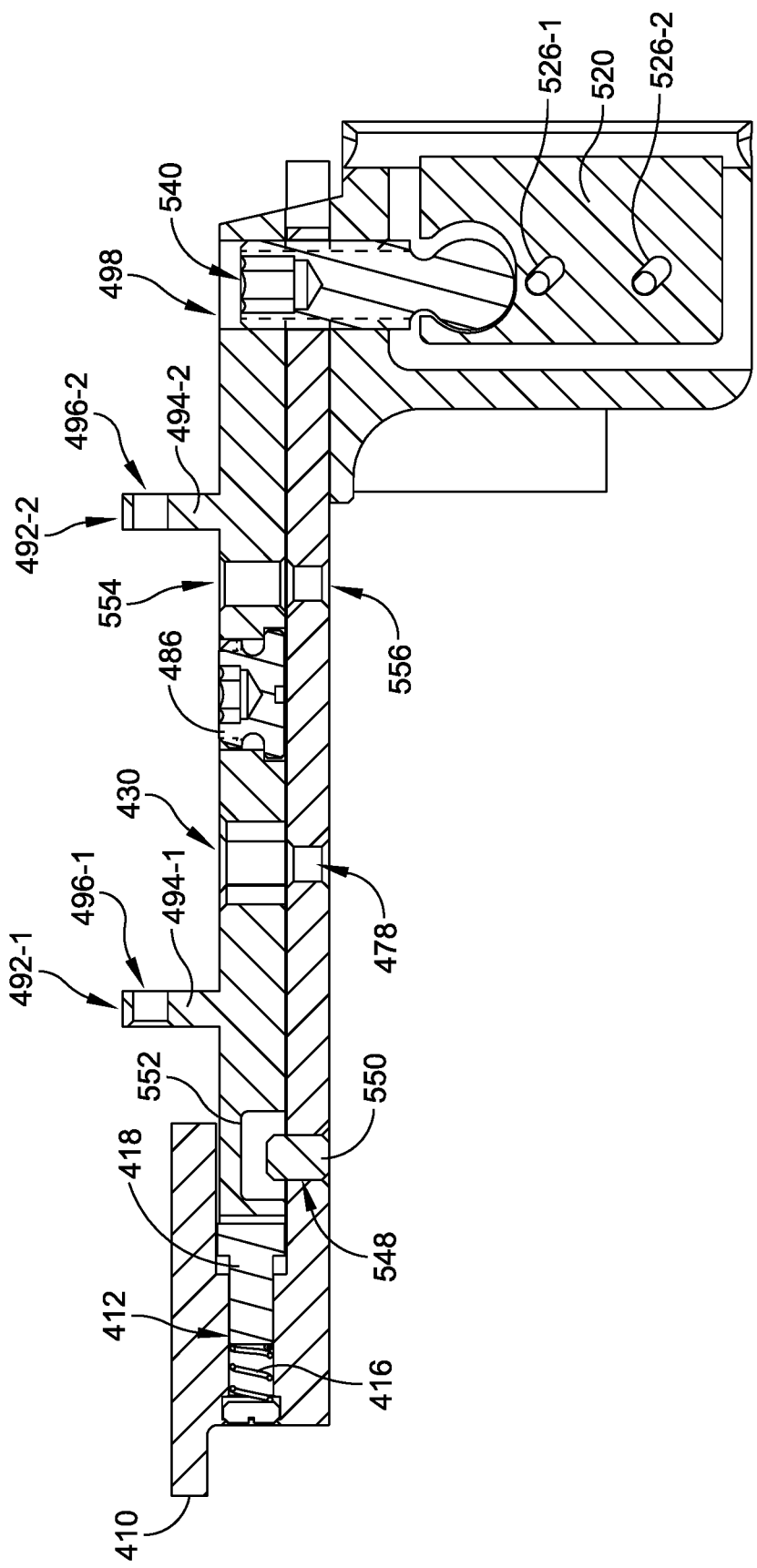
FIG. 14 is a sectional view of the alignment guide illustrated in FIG. 11 taken along line 14-14 in FIG. 13 in accordance with some embodiments.

As best seen in FIG. 12, base 402 may have a generally rectangular shape without oblong sections and sets of interconnected holes as provided by base 102. Instead, the base 402 may include a hole 548 that is sized and configured to receive a dowel or other type of pin 550 therein. Pin 550 may be sized and configured to be received within a slot 552 as best seen in FIG. 14. The combination of slot 552 and pin 550 constrains the relative movement between swing arm 450 relative to base 402 to a predefined distance.

Figure 13:
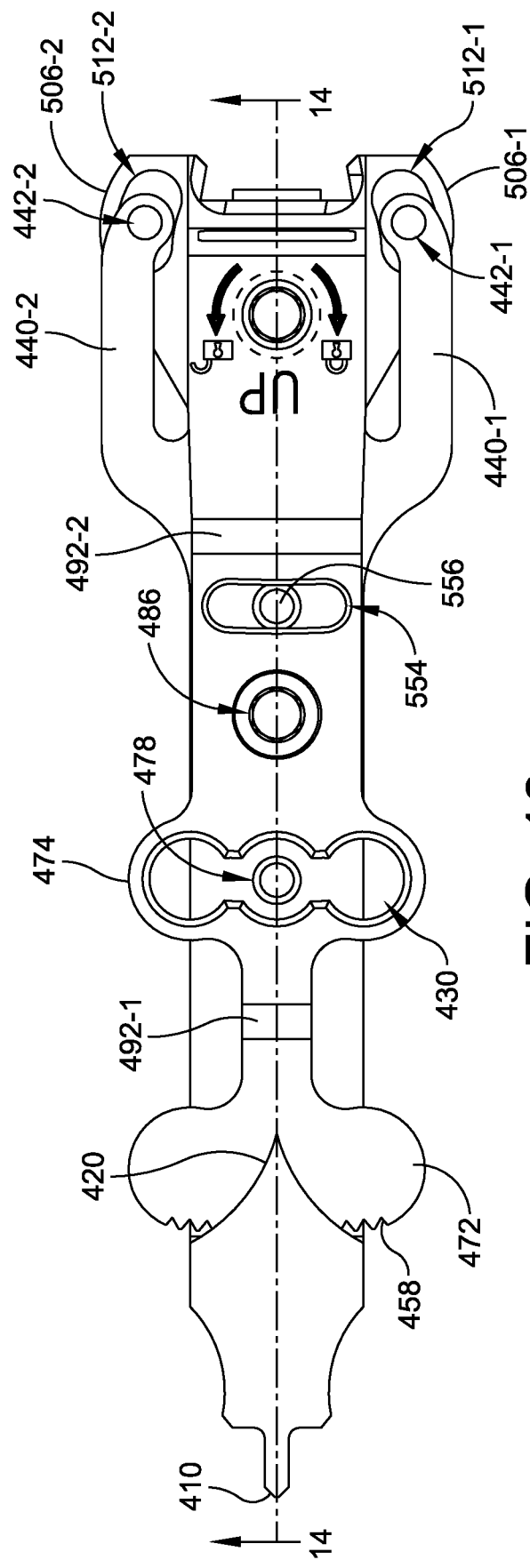
FIG. 13 is a top side plan view of the alignment guide illustrated in FIG. 11 in accordance with some embodiments.

Oblong section 474 of swing arm 450 may include a set of interconnected holes 430 that are aligned with a hole 478 defined by base 402. Swing arm 450 may also define a slot 554 that may be aligned with a hole 556 defined by base 402 as best seen in FIGS. 13-14. Thus, a person of ordinary skill in the art will understand that the arrangement of holes and slots provided by the base and swing arm may be varied.

Figure 15:
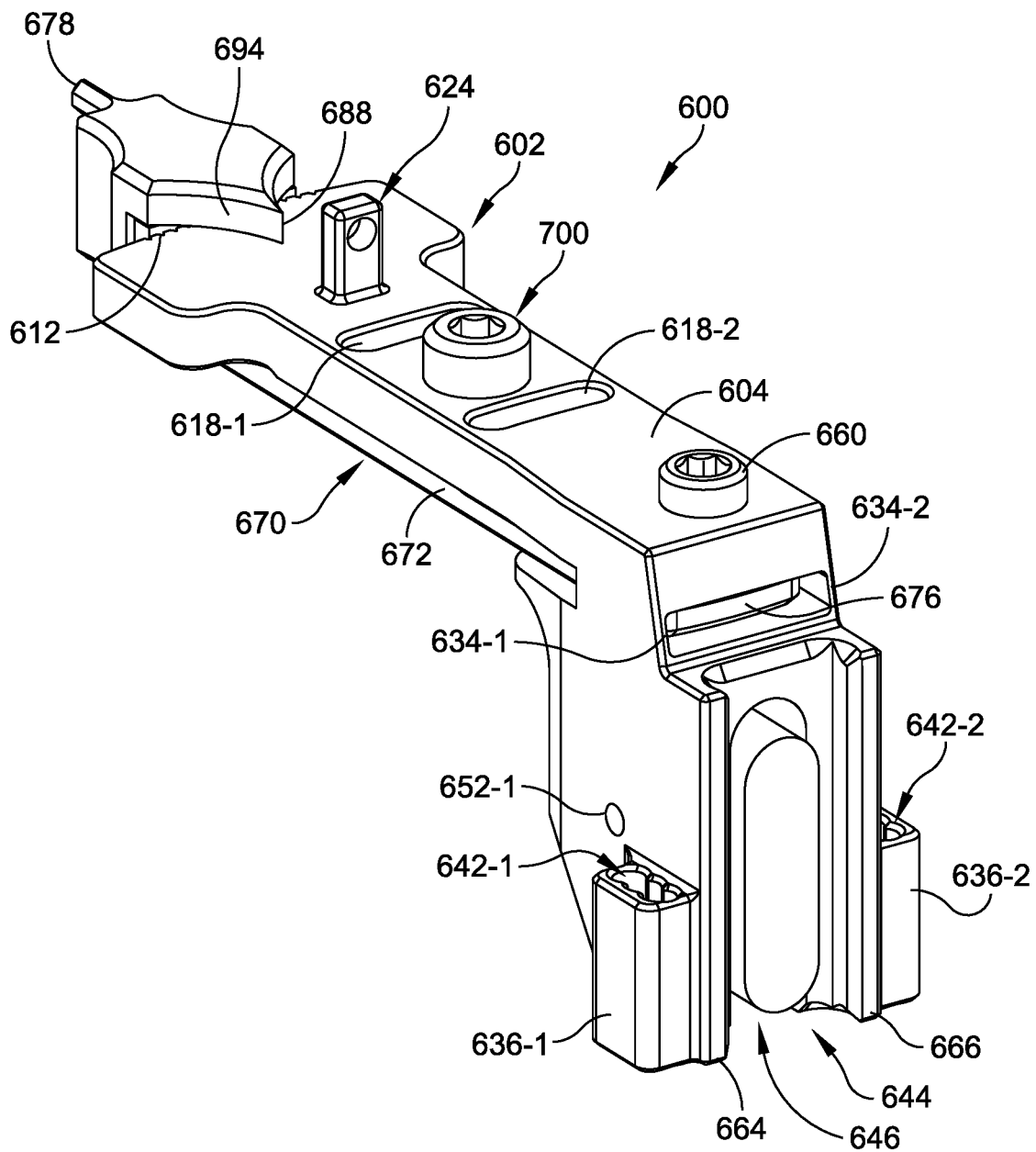
FIG. 15 is a perspective view of another example of an alignment guide in accordance with some embodiments.
Figure 16:
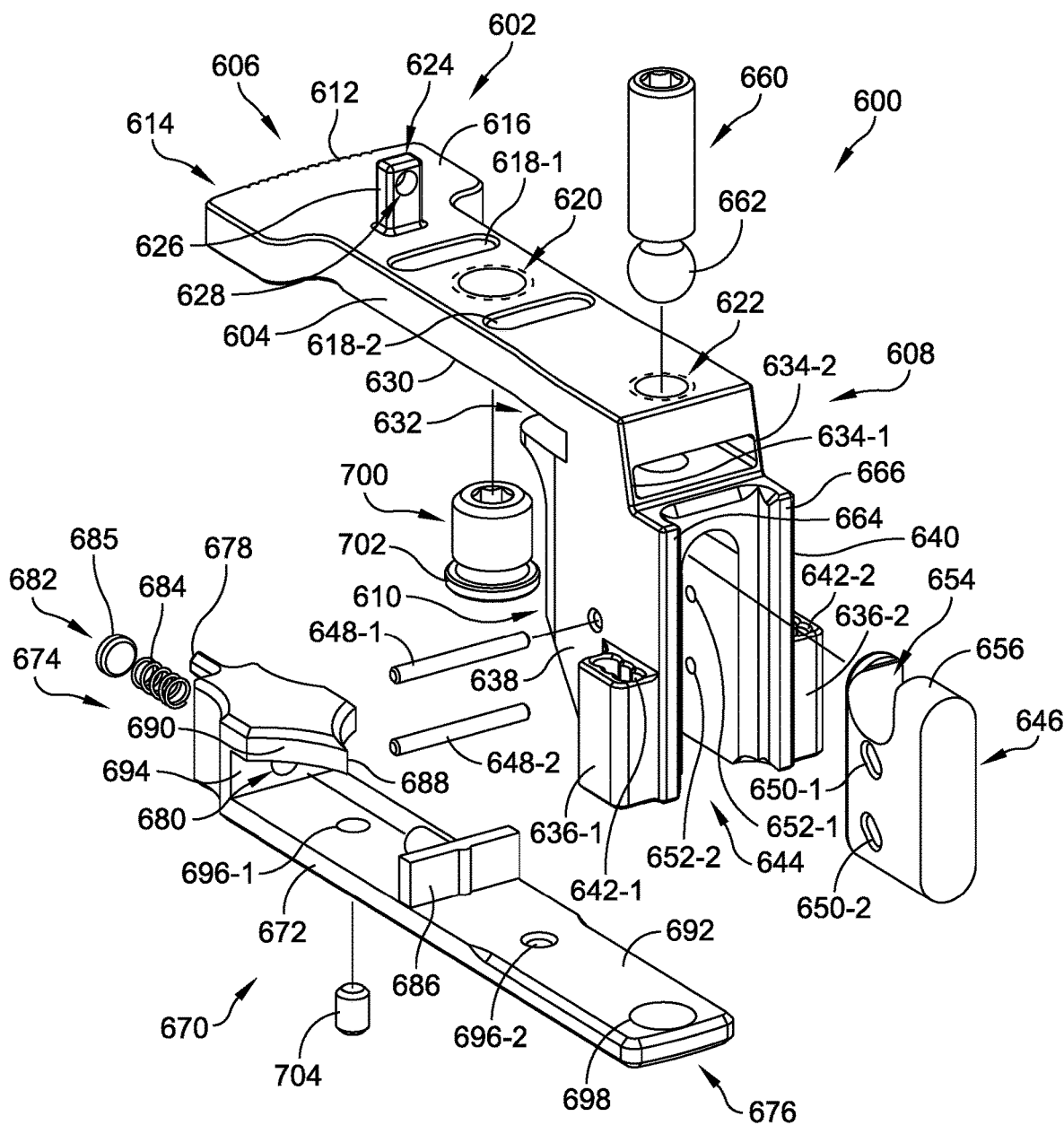
FIG. 16 is an exploded perspective view of the alignment guide illustrated in FIG. 15 in accordance with some embodiments.

FIGS. 15 and 16 illustrate another example of an alignment guide in accordance with some embodiments. Alignment guide 600 may include a base 602 that may be coupled to a swing arm 670. Base 602 may have an elongate body 604 extending from a first end 606 to a second end 608. A housing 610 may be provided at the second end 608. First end 606 of body 604 may include a number of teeth 612 arranged along a front edge 614. Teeth 612 may be sized and configured to be engaged by a spring-biased detent 682 of swing arm 670 as described below. Indicia (not shown in FIGS. 16-17) may be provided on upper surface 616 of body 604 adjacent to teeth 612 for providing a visual indicator to a user as to the desired angular offset as also be described below.

Body 604 may define a first and second slots 618-1, 618-2 (collectively, "slots 618") that extend in a widthwise direction across body 604 and extend entirely through body 604. In some embodiments, a hole 620, which may be threaded, is defined by body 604 between slots 618. Hole 620 is sized and configured to receive a locking screw 700 therein. Body 604 may also define a hole 622, which may be threaded, adjacent to end 608. In some embodiments, body 604 includes a pin holder 624 extending upwards from upper surface 616. Pin holder 624 may include a projection 626 that defines a hole 628 that is sized and configured to receive an elongate radiopaque member, such as a k-wire or pin, as will be understood by one of ordinary skill in the art. Pin holder 624 may be positioned such that a central axis defined by hole 628 aligns with a longitudinal axis defined by the elongate body 604 of base 602.

Housing 610 may extend from lower surface 630 of body 604. In some embodiments, a gap 632 is provided between the lower surface 630 of body 604 and housing 610 such that housing 610 is coupled to body 604 by one or more appendages 634-1, 634-2 (collectively, "appendages 634"). Gap 632 is dimensioned to receive the body 672 of swing arm 670 in sliding engagement as described below and shown in FIG. 15. In some embodiments, housing 610 includes first and second wings 636-1, 636-2 (collectively, "wings 636") that extend outwardly from opposed sides 638, 640 of housing 610. Each wing 636-1, 636-2 may define a plurality of interconnected holes 642-1, 642-2 (collectively, "holes 642"). It should be understood that although a plurality of interconnected holes 642 are shown, the plurality of holes 642 may be implemented as unconnected (i.e., separate) holes, as a single hole, or as a slot. In some embodiments, holes 642 are arranged such that they extend perpendicular to the longitudinal axis defined by the elongate body 604 of base 602, although one of ordinary skill in the art will understand that holes 642 may be arranged or oriented at other angles with respect to the longitudinal axis defined by elongate body 604 of base 602.

Housing 610 may define a chamber 644 that extends inwardly between sides 638, 640 and is in communication with hole 622. Chamber 644 may be sized and configured to receive a locking block 646, which may be secured within chamber 644 via pins 648-1, 648-2 (collectively, "pins 648") that are received within slots 650-1, 650-2 (collectively, "slots 650") defined by locking block 646 and holes 652-1, 652-2 (collectively, "holes 652") defined by housing 610. Locking block 646 may define a contoured (e.g., oblong) cavity 654 that extends inwardly from side 656. Cavity 654 may be contoured to facilitate engagement between locking block 646 and the ball head 662 of locking screw 660. The combination of slots 650 and contoured cavity 654 enables locking block 646 to move relative to housing 610 and facilitate the locking of a sizing and/or cutting guide to the guide 600 as described below.

Housing 610 may include a pair of spaced apart rails 664, 666 each defining a respective undercut for forming a dovetail connection with a cutting guide, such as with the dovetail extension 394 of coronal sizing and drill guide 380 described in the '904 patent previously incorporated by reference herein. A person of ordinary skill in the art will understand that housing 610 may include connection mechanisms other than a dovetail connection for coupling the guide 600 to one or more sizing and/or cutting guides.

Swing arm 670 may have an elongate body 672 extending from a first end 674 to a second end 676. First end 674 may terminate in one or more points 678 or other features for providing an indication of direction as will be understood by one or ordinary skill in the art. A hole or cavity 680 sized and configured to receive a spring-biased detent 682 may be defined adjacent to end 674. Spring-biased detent 682 may include a biasing member 684, a cap 685, and a detent body 686 as best seen in FIG. 16. In some embodiments, the spring-biased detent 682 is configured to provide audible and/or tactile feedback to a user indicating the angular adjustment of guide 600 as described in greater detail below.

First end 674 may also include a second point or indicator 688 that is aligned with point 678, but points in the opposite direction. As best seen in FIG. 16, indicator 688 may be positioned on a ledge 690 that is located above an upper surface 692. The hole or cavity 680 extends inwardly from vertical surface 694 and between ledge 690 and upper surface 692. Body 672 of swing arm 670 may define first and second holes 696-1, 696-2 (collectively, "holes 696") that are positioned along body 672 such that they are aligned with slots 618 when swing arm 670 is coupled to base 602. Body 672 may also define a hole 698 that is sized and configured to provide clearance for locking screw 660 and is positioned along body 672 to be aligned with hole 622 defined by base 602.

Guide 600 may be assembled by threading locking screw 700 into hole 620 defined by body 604 of base 602. Although not shown in FIGS. 15 and 16, hole 620 may include an undercut section, like undercut section 182 of hole 180 shown in FIG. 4, so that flange 702 of locking screw 700 may be received within the undercut section. Body 672 of swing arm 670 may be placed into abutment with the body 604 of base 602 and end 676 of swing arm 670 may be inserted into gap 632 between body 604 and housing 610 such that hole 698 is aligned with hole 622. With holes 622, 698 aligned with one another, ball head 662 of locking screw 660 may be placed within cavity 654 of locking block 646, then locking screw 660 may be threaded into hole 622. Locking block 646 may be pinned to housing 610 by inserting pins 648 into holes 652 and through slots 650. In some embodiments, a dowel pin 704 may be received within a hole defined by swing arm 670 in a press-fit engagement and received within a cavity or slot formed in the bottom surface of body 604 of base 602 to limit the rotational movement of swing arm 670 relative to base 602 as will be understood by one of ordinary skill in the art.

In use, a surgeon or other individual may place one or more pins or k-wires in the anterior surface of a patient's tibia based on the use of a patient-specific mount, such as patient-specific mount 3000 and pins 3010 described in the '904 patent. With pins inserted in the patient, the patient-specific mount is removed from its engagement with the pins and the alignment guide 600 is the placed on the pins. More particularly, pins 3010 may be received within holes 642 defined by wings 636 of base 602.

With alignment device 600 coupled to pins 3010, a surgeon or other individual may check to confirm a cutting guide will be properly oriented and/or adjust the alignment of a cutting guide. For example, varus/valgus adjustment may be made by rotating swing arm 670 relative to base 602. As noted above, the swing arm 670 is able to rotate relative to base 602 about an axis defined by holes 622, 698 in which locking screw 660 is received. Rotation and relative movement between swing arm 670 and base 602 is permitted by slots 618 and a cavity or slot formed in the bottom surface of body 604 of base 602 in which dowel 704 is received.

As swing arm 670 moves relative to base 602, spring-biased detent 682 provides audible and/or tactile feedback as detent 686 engages teeth 612 (and the troughs between teeth 612). Further, indicia, if provided, indicate the amount of varus/valgus adjustment (e.g., 1°, 2°, etc.) based on movement of the swing arm 670 relative to the base 602. When the desired adjustment has been achieved, the position of swing arm 670 may be fixed using locking screw 700. Rotation of screw 700 in a first direction (e.g., clockwise direction) may lock the position of swing arm 670 to base 602, and rotation of screw 700 in a second direction (e.g., counter-clockwise direction) may permit relative movement of swing arm 670 to base 602.

It should be appreciated that a guide, such as a coronal sizing and drill guide 380 or cutting guide as described in the '904 patent, may be coupled to alignment guide 600 prior to or after the angular adjustment is performed. Such a guide may be coupled to alignment guide 600 by inserting a dovetail extension into the corresponding dovetail/undercuts provided by rails 664, 666 of housing 610. The cutting or drill guide may be locked to the housing 610 by rotating locking screw 660 in a first direction (e.g., counter-clockwise). The unlocking is provided by the ball head 662 engaging the surface(s) defining cavity 654 of locking block 646, which causes locking block 646 to be pulled inwardly into chamber 644 guided by the engagement of pins 648 and slots 650 decoupling alignment guide 600 from the cutting and/or drill guide. Rotating the locking screw 660 in a second, opposite direction (e.g., clockwise) results in the locking of the cutting and/or drill guide from alignment guide 600, such that the alignment guide 600 may be coupled to the cutting and/or drill guide. For example, the dovetail connection between the alignment guide 600 and the cutting and/or drill guide may be engaged by sliding the alignment guide 600 relative to the cutting and/or drill guide.

The swing arm 670 may be locked in position relative to the bone of the patient by inserting pins or wires through holes 696 defined by swing arm 670 (and thus also through slots 618 defined by base 602). With swing arm 670 pinned to the patient's bone, one or more pins may be removed from the holes 642 defined by wings 636 of base 602 so that base 602 may be repositioned (e.g., such that the elongate body 604 of base 602 is parallel to elongate body 672 of swing arm 670).

If desired, an elongate radiopaque member, such as a k-wire or pin, may be inserted through hole 628 defined by pin holder 624 to provide for a fluoroscopic check. Under fluoroscopy, a surgeon or other individual may check to determine whether the radiopaque member 3004 is aligned with a mechanical and/or longitudinal axis defined by a bone, such as the tibia, of the patient. A person of ordinary skill in the art will understand that the fluoroscopic check may be performed before or after the cutting and/or drill guide is coupled to the alignment guide 600.

As detailed above, in some embodiments, an alignment guide includes a base, a swing arm for coupling to the base such that the swing arm is movable relative to the base, and a locking device for selectively fixing a position of the swing arm relative to the base. The base defines at least one first hole sized and configured to receive a first fixation element and defines at least one second hole sized and configured to receive a second fixation element. The swing arm extends from a first end to a second end. The second end of the swing arm including a coupling mechanism for coupling another guide to the second end of the swing arm.

In some embodiments, the second end of the swing arm includes a housing defining a chamber for receiving a locking block therein. The locking block is sized and configured to move within the chamber for coupling another guide to the second end of the swing arm.

In some embodiments, the locking block defines a cavity sized and configured to receive a screw therein.

In some embodiments, the base includes at least one first arm and at least one second arm. The at least one first arm and at least one second arm are spaced apart from one another such that the housing of the swing arm may be received between the at least one first arm and the at least one second arm.

In some embodiments, the at least one first arm defines the at least one first hole and the at least one second arm defines the at least one second hole.

In some embodiments, the housing defines a first slot and a second slot. The first slot is positioned relative to the housing such that when the swing arm is coupled to the base the first slot is at least partially aligned with the at least one first hole. The second slot is positioned relative to the housing such that when the swing is coupled to the base the second slot is at least partially aligned with the at least one second hole.

In some embodiments, the base supports a spring-loaded detent that is configured to engage a plurality of teeth located at the first end of the swing arm and provide an audible and/or a tactile indication when the swing arm is moved relative to the base.

In some embodiments, an upper surface of the swing arm includes indicia for indicating an angular adjustment.

In some embodiments, at least one pin holder extends from an upper surface of the swing arm. The at least one pin holder is sized and configured to support an elongate radiopaque member.

In some embodiments, the locking device includes a locking screw.

In some embodiments, the locking screw is sized and configured to be received in a hole defined by the swing arm.

In some embodiments, a method includes positioning an alignment guide relative to a bone, adjusting a position of a swing arm of the alignment guide while a position of a base of the alignment guide remains fixed relative to the bone, fixing the position of the swing arm relative to the base, and coupling a second guide to the alignment guide.

In some embodiments, positioning the alignment guide relative to the bone includes sliding the alignment guide onto first and second pins previously inserted into bone.

In some embodiments, a method includes placing a patient-specific guide onto a surface of the bone and inserting the first and second pints into the bone.

In some embodiments, the first pin is received within a first hole defined by the swing arm of the alignment guide, and the second pin is received within a second hole defined by the swing arm of the alignment guide.

In some embodiments, fixing the position of the swing arm relative to the base includes rotating a lock screw.

In some embodiments, a method includes coupling a radiopaque member to at least one pin holder extending from an upper surface of the swing arm.

In some embodiments, a method includes decoupling the alignment guide from the second guide and removing the alignment guide from the first and second pins while leaving the second guide secured to the bone.

In some embodiments, decoupling the alignment guide from the second guide includes rotating a locking screw and disengaging a dovetail connection between the alignment guide and the second guide.

In some embodiments, when the position of the swing arm is adjusted, a spring-loaded detent selectively engages teeth formed on an end of the swing arm thereby providing an audible and/or a tactile feedback to a user.

Although the guides, systems, and methods have been described in terms of exemplary embodiments, they are not limited thereto. Rather, the appended claims should be construed broadly, to include other variants and embodiments of the guides, systems, and methods, which may be made by those skilled in the art without departing from the scope and range of equivalents of the invention.

What is claimed is:

1. An alignment guide, comprising:
   a base defining at least one first hole sized and configured to receive a first fixation element and defining at least one section hole sized and configured to receive a second fixation element and including at least one first arm and at least one second arm, the at least one first arm and at least one second arm being spaced apart from one another; and
   a swing arm for coupling to the base such that the swing arm is movable relative to the base, the swing arm extending from a first end to a second end, the second end of the swing arm including a coupling mechanism for coupling another guide to the second end of the swing arm and a housing defining a chamber for receiving a locking block therein, the locking block sized and configured to move within the chamber for coupling another guide to the second end of the swing arm such that the housing of the swing arm may be received between the at least one first arm and the at least one second arm; and
   a locking device for selectively fixing a position of the swing arm relative to the base.

2. The alignment guide of claim 1, wherein the locking block defines a cavity sized and configured to receive a screw therein.

3. The alignment guide of claim 1, wherein the at least one first arm defines the at least one first hole and the at least one second arm defines the at least one second hole.

4. The alignment guide of claim 3, wherein the housing defines a first slot and a second slot, the first slot positioned relative to the housing such that when the swing arm is coupled to the base the first slot is at least partially aligned with the at least one first hole, and the second slot positioned relative to the housing such that when the swing is coupled to the base the second slot is at least partially aligned with the at least one second hole.

5. The alignment guide of claim 1, wherein the base supports a spring-loaded detent that is configured to engage a plurality of teeth located at the first end of the swing arm and provide at least one of an audible or a tactile indication when the swing arm is moved relative to the base.

6. The alignment guide of claim 5, wherein an upper surface of the swing arm includes indicia for indicating an angular adjustment.

7. The alignment guide of claim 1, wherein the locking device includes a locking screw.

8. The alignment guide of claim 7, wherein the locking screw sized and configured to be received in a hole defined by the swing arm.

9. An alignment guide comprising:
   a base defining at least one first hole sized and configured to receive a first fixation element and defining at least one section hole sized and configured to receive a second fixation element;
   a swing arm for coupling to the base such that the swing arm is movable relative to the base, the swing arm extending from a first end to a second end, the second end of the swing arm including a coupling mechanism for coupling another guide to the second end of the swing arm wherein at least one pin holder extends from an upper surface of the swing arm, the at least one pin holder sized and configured to support an elongate radiopaque member; and
   a locking device for selectively fixing a position of the swing arm relative to the base.

10. A method, comprising:
providing an alignment guide including a base defining at least one first hole sized and configured to receive a first fixation element and defining at least one section hole sized and configured to receive a second fixation element, a swing arm for coupling to the base such that the swing arm is movable relative to the base, the swing arm extending from a first end to a second end, the second end of the swing arm including a coupling mechanism for coupling another guide to the second end of the swing arm wherein at least one pin holder extends from an upper surface of the swing arm, the at least one pin holder sized and configured to support an elongate radiopaque member and a locking device for selectively fixing a position of the swing arm relative to the base;
positioning an alignment guide relative to a bone;
adjusting a position of a swing arm of the alignment guide while a position of a base of the alignment guide remains fixed relative to the bone;
fixing the position of the swing arm are relative to the base; and
coupling a second guide to the alignment guide.

11. The method of claim 10, wherein positioning the alignment guide relative to the bone includes sliding the alignment guide onto first and second pins previously inserted into the bone.

12. The method of claim 11, further comprising:
placing a patient-specific guide onto a surface of the bone; and
inserting the first and second pints into the bone.

13. The method of claim 11, wherein the first pin is received within a first hole defined by the swing arm of the alignment guide and the second pin is received within a second hole defined by the swing arm of the alignment guide.

14. The method of claim 10, wherein fixing the position of the swing arm relative to the base includes rotating a lock screw.

15. The method of claim 10, further including coupling a radiopaque member to at least one pin holder extending from an upper surface of the swing arm.

16. The method of claim 10, wherein securing the second guide to bone includes inserting at least one third pin into a hole defined by the second guide.

17. The method of claim 10, further comprising:
decoupling the alignment guide from the second guide; and
removing the alignment guide from the first and second pins while leaving the second guide secured to the bone.

18. The method of claim 17, wherein decoupling the alignment guide from the second guide includes:
rotating a locking screw; and
disengaging a dovetail connection between the alignment guide and the second guide.

19. The method of claim 10, wherein, when the position of the swing arm is adjusted, a spring-loaded detent selectively engages teeth formed on an end of the swing arm thereby providing at least one of audible and a tactile feedback to a user.

20. A method, comprising:
positioning an alignment guide relative to a bone, the alignment guide including a base, defining at least one first hole sized and configured to receive a first fixation element and defining at least one section hole sized and configured to receive a second fixation element, a swing arm for coupling to the base such that the swing arm is movable relative to the base, the swing arm extending from a first end to a second end, the second end of the swing arm including a coupling mechanism for coupling another guide to the second end of the swing arm wherein at least one pin holder extends from an upper surface of the swing arm, the at least one pin holder sized and configured to support an elongate radiopaque member; a locking device for selectively fixing a position of the swing arm relative to the base;
adjusting a position of the swing arm of the alignment guide while the position of the base of the alignment guide remains fixed relative to the bone;
fixing the position of the swing arm are relative to the base; and
coupling a second guide to the alignment guide.

* * * * *